United States Patent
Boyce et al.

(10) Patent No.: US 10,570,102 B2
(45) Date of Patent: Feb. 25, 2020

(54) SYNTHESIS OF BENZODIAZEPINE DERIVATIVES

(71) Applicant: Trio Medicines Limited, Brighton East Sussex (GB)

(72) Inventors: Malcolm James Boyce, London (GB); Liv Thomsen, London (GB); Donald Alan Gilbert, Ipswich (GB); David Wood, Sudbury Suffolk (GB)

(73) Assignee: TRIO MEDICINES LIMITED, Brighton East Sussex (GB)

( * ) Notice: Subject to any disclaimer, the term of this patent is extended or adjusted under 35 U.S.C. 154(b) by 0 days.

(21) Appl. No.: 15/750,339

(22) PCT Filed: Aug. 5, 2016

(86) PCT No.: PCT/GB2016/052442
§ 371 (c)(1),
(2) Date: Feb. 5, 2018

(87) PCT Pub. No.: WO2017/025727
PCT Pub. Date: Feb. 16, 2017

(65) Prior Publication Data
US 2018/0237400 A1 Aug. 23, 2018

Related U.S. Application Data

(63) Continuation of application No. PCT/GB2015/052291, filed on Aug. 7, 2015.

(30) Foreign Application Priority Data

Aug. 7, 2015 (GB) .................................. 1513979.3

(51) Int. Cl.
*C07D 243/26* (2006.01)
*C07D 401/04* (2006.01)
*C07C 259/10* (2006.01)
*C07C 271/28* (2006.01)

(52) U.S. Cl.
CPC .......... *C07D 243/26* (2013.01); *C07C 259/10* (2013.01); *C07C 271/28* (2013.01); *C07D 401/04* (2013.01)

(58) Field of Classification Search
CPC .......................... A61K 31/5513; C07D 487/04
See application file for complete search history.

(56) References Cited

U.S. PATENT DOCUMENTS

| 4,820,834 A | 4/1989 | Evans et al. |
| 5,563,136 A | 10/1996 | Capet et al. |

FOREIGN PATENT DOCUMENTS

| EP | 167919 | * | 1/1986 |
| EP | 0434369 A1 | | 6/1991 |
| EP | 0490590 A1 | | 6/1992 |
| EP | 1 342 719 A1 | | 9/2003 |
| WO | 1993/008175 A1 | | 4/1993 |
| WO | 1993/016999 A1 | | 9/1993 |
| WO | 199319063 A1 | | 9/1993 |
| WO | 1994/024151 A1 | | 10/1994 |
| WO | 9506040 A1 | | 3/1995 |
| WO | 9506041 A1 | | 3/1995 |
| WO | 1998/015535 A1 | | 4/1998 |
| WO | 2003041714 A1 | | 5/2003 |
| WO | 2004101533 A1 | | 11/2004 |
| WO | 2016/020698 A1 | | 2/2016 |

OTHER PUBLICATIONS

Sigma-Aldrich, now Millipore Sigma (https://www.sigmaaldrich.com/chemistry/chemical-synthesis/learning-center/chemfiles/chemfile-2001-2003/vol-2-no-7/phosgene-and-substitutes.html, downloaded Jan. 5, 2019, p. 2).*
Berna, M.J. et al. (2007) "Role of CCK/gastrin receptors in gastrointestinal/metabolic diseases and results of human studies using gastrin/CCK receptor agonists/antagonists in these diseases," Curr Top Med Chem. 2007; 7(12):1211-1231.
Boyce, M. et al. (2013) "Netazepide, a gastrin/CCK2 receptor antagonist, causes dose-dependent, persistent inhibition of the responses to pentagastrin in healthy subjects," Br J Clin Pharmacol, 76:5, 689-698.
Bock et al. (1993) "Development of 1,4-benzodiazepine cholecystokinin type B antagonists," J. Med. Chem. 36(26):4276-4292.
Kramer et al. (1995) "A placebo-controlled trial of L-365,260, a CCK-B antagonist, in panic disorder," Biol. Psychiatry. 37(7):462-466.
Murphy et al. (1993) "The gastrin-receptor antagonist L-365,260 inhibits stimulated acid secretion in humans," Clin. Pharmacol. Ther. 54(5):533-539.
Semple et al. (1997) "(3R)-N-(1-(tert-butylcarbonylmethyl)-2,3-dihydro-2-oxo-5-(2-pyridyl)-1H-1,4-benzodiazepin-3-yl)-N'-(3-(methylamino)phenyl)urea(YF476): a potent and orally active gastrin/CCK-B antagonist," J. Med. Chem. 40(3):331-341.
Yano et al. (1996) "In Vitro Stability and in Vivo Absorption Studies of Colloidal Particles Formed from a Solid Dispersion System," Chem. Pharm. Bull. (Tokyo). 44(12):2309-2313.

(Continued)

*Primary Examiner* — Susanna Moore
(74) *Attorney, Agent, or Firm* — Brian C. Trinque; Lathrop GPM LLP

(57) ABSTRACT

The invention relates to processes for the synthesis of benzodiazepine derivatives of Formula I: (I)

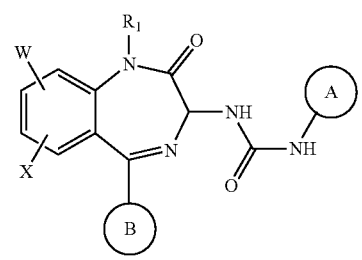

24 Claims, No Drawings

(56) References Cited

OTHER PUBLICATIONS

International Search Report with Written Opinion corresponding to International Patent Application No. PCT/GB2016/052442, dated Oct. 24, 2016.
Search Report corresponding to Great Britain Patent Application No. 1513979.3, dated May 24, 2016.

* cited by examiner

SYNTHESIS OF BENZODIAZEPINE DERIVATIVES

CROSS-REFERENCE TO RELATED APPLICATIONS

This application is a 35 U.S.C. § 371 filing of International Application No. PCT/GB2016/052442, filed on Aug. 5, 2016, which claims priority to PCT/GB2015/052291, filed Aug. 7, 2015, and Great Britain patent application number 1513979.3 filed Aug. 7, 2015. The entire contents of these applications are incorporated by reference herein, in their entirety.

FIELD OF THE INVENTION

The invention relates to the synthesis of benzodiazepine derivatives.

BACKGROUND

Benzodiazepine derivatives such as YF476 act as an antagonists at gastrin/$CCK_2$ receptors (Semple et al. J Med Chem 1997; 40: 331-341).

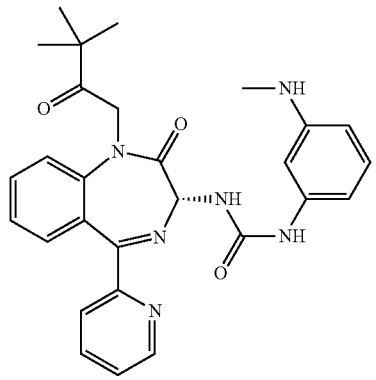

YF476

Further benzodiazepine derivatives are described in WO93/16999, Yano et al. Chem Pharm Bull (Tokyo) 1996; 44: 2309-2313, Murphy et al. Clin Pharmacol Ther 1993; 54: 533-39 and Kramer et al. Biol Psychiatry 1995; 37: 462-466.

The synthesis of the type of benzodiazepine derivatives described in Semple et al. involves coupling of an isocyanate, for example 3-[N-(tert-butyloxycarbonyl)methylamino]phenyl isocyanate, with an amine, for example (R)-3-amino-1[(tert-butylcarbonyl)-methyl]-2,3-dihydro-5-(2-pyridyl)-1H-1,4-benzodiazepin-2-one. The isocyanate is prepared using potentially explosive azide chemistry.

There remains a need for improved synthetic processes for the production of this type of benzodiazepine derivatives which avoid the need for potentially explosive azide chemistry. In addition, there remains a need for efficacious gastrin/cholecystokinin 2 ($CCK_2$) receptor antagonists which can successfully be used in pharmaceutical compositions to provide beneficial properties in terms of pharmacokinetics, improved bioavailability, avoidance of a requirement for administration with food, minimisation of processing steps required in formulation, and the like.

SUMMARY OF THE INVENTION

In a first aspect, the present invention provides a process for producing a compound of formula (I):

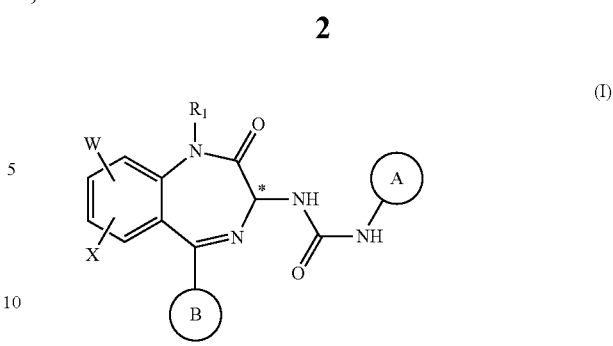

or a pharmaceutically acceptable salt thereof, wherein
$R_1$ is:
(i) —$CH_2C(O)C(R_2)(R_3)$-L-$R_4$ or —$CH_2CHOHC(R_2)$ $(R_3)$-L-$R_4$, in which:
$R_2$ and $R_3$ are each, independently, H or $C_{1-3}$ aliphatic, halo, or $C_{1-3}$ haloaliphatic, or wherein $R_2$ and $R_3$ together with the intervening carbon atom to which they are bonded, form a $C_{3-6}$ carbocyclic moiety;
L is a bond or $C_{1-3}$ alkylene; and
$R_4$ is —$OR_5$ or —$SR_5$, wherein $R_5$ is hydrogen, optionally substituted alkyl (e.g. $C_{1-6}$ alkyl, such as methyl), a protecting group or —$C(O)R_6$, wherein $R_6$ is optionally substituted aliphatic, heteroaliphatic, aromatic or heteroaromatic moiety;
(ii) —$CH_2CHOH(CH_2)_aR_7$ or —$CH_2C(O)(CH_2)_aR_8$ in which a is 0 or 1 and $R_7$ and $R_8$ are selected from alkyl and cycloalkyl groups and saturated heterocyclic groups optionally substituted at a hetero-atom; or
(iii) an optionally substituted aliphatic moiety;
W and X are, independently, hydrogen, halo, $C_{1-8}$ alkyl or $C_{1-8}$ alkoxy; and
rings A and B are each, independently, a monocyclic aryl or heteroaryl, optionally substituted with one or more substituents independently selected from halo, hydroxy, amino, nitro, carboxyl, carboxamido, cyano, —$SO_3H$, and optionally substituted $C_{1-8}$ alkyl, $C_{1-8}$ alkoxy, $C_{1-8}$ alkylamino or di($C_{1-8}$ alkyl)amino,
wherein any one or more substituent on $R_1$, ring A or ring B may be unprotected or in a protected form;
wherein the process comprises:
(a) providing a reaction mixture by adding a compound of formula (I-A), a compound of formula (I-B) and a phosgene synthetic equivalent or phosgene to an aprotic solvent, to form a compound of formula (I)

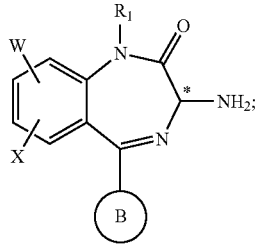

or (b) providing a reaction mixture by adding a compound of formula (I-C), and a phosgene synthetic equivalent or phosgene, to an aprotic solvent and, subsequently, adding a compound of formula (I-B) to the reaction mixture to form a compound of formula (I):

(I-C)

wherein the phosgene synthetic equivalent is carbonyldiimidazole (CDI), diphosgene, triphosgene, a chloroformate (e.g. 4-nitrophenyl chloroformate) or disuccinimidyl carbonate.

The phosgene synthetic equivalent or phosgene may, for example, be CDI.

In some embodiments, the process comprises the additional step of deprotection to remove one or more protecting groups wherein any one or more substituents on $R_1$, ring A or ring B is in a protected form. For example, as indicated above protecting groups may be present on any one or more substituent on $R_1$, ring A or ring B in the compound of formula (I-A), (I-B) or (I-C) and, in these embodiments, the process may comprise the additional step of deprotection to remove the one or more protecting groups to form a compound of formula (I), or any embodiment thereof as described herein. Thus, the process may comprise providing a reaction mixture by adding a compound of formula (I-A), a compound of formula (I-B) and a phosgene synthetic equivalent or phosgene to an aprotic solvent, to form a compound of formula (I) via initial formation of a protected compound (I) and the additional step of deprotection to remove one or more protecting groups to form a compound of formula (I); or providing a reaction mixture by adding a compound of formula (I-C), and a phosgene synthetic equivalent or phosgene, to an aprotic solvent and, subsequently, adding a compound of formula (I-B) to the reaction mixture to form a compound of formula (I) via initial formation of a protected compound (I) and the additional step of deprotection to remove one or more protecting groups to form a compound of formula (I)

In some embodiments, wherein the process comprises step (a) of providing a reaction mixture by adding a compound of formula (I-A), a compound of formula (I-B) and a phosgene synthetic equivalent or phosgene to an aprotic solvent, to form a compound of formula (I), the reaction mixture is maintained at a temperature of no more than 50° C., no more than 40° C. or preferably no more than 30° C.

Wherein the process comprises step (a) of providing a reaction mixture by adding a compound of formula (I-A), a compound of formula (I-B) and a phosgene synthetic equivalent or phosgene to an aprotic solvent, to form a compound of formula (I), the compound of formula (I-A), the compound of formula (I-B) and the phosgene synthetic equivalent or phosgene may be added to the solvent in any order. Addition of these compounds to provide a reaction mixture results in reaction in the reaction mixture to form a compound of formula (I). Preferably the compound of formula (I-A) and the phosgene synthetic equivalent or phosgene are added to the solvent prior to addition of the compound of formula (I-B). In some embodiments, the temperature of the reaction mixture is maintained at a temperature of 0-10° C., preferably 0-5° C., during addition of the compound of formula (I-A) and the phosgene synthetic equivalent or phosgene to the solvent. During subsequent addition of the compound of formula (I-B), the reaction mixture is preferably maintained at a temperature no more than 30° C., for example at 15-20° C.

In step (a) the aprotic solvent may, for example, be dichloromethane, acetonitrile or toluene, preferably dichloromethane.

Wherein the process comprises step (b) of providing a reaction mixture by adding a compound of formula (I-C) and a phosgene synthetic equivalent or phosgene, to an aprotic solvent and, subsequently, adding a compound of formula (I-B) to the reaction mixture, addition of these compounds results in reaction in the reaction mixture to form a compound of formula (I). The process of step (b) may comprise heating the reaction mixture to a temperature of at least 40° C., preferably at least 50° C., before addition of the compound of formula (I-B). The process of step (b) may, as an alternative to heating, comprise adding a non-aqueous base to the reaction before addition of the compound of formula (I-B).

In step (b) the aprotic solvent may, for example, be dichloromethane, acetonitrile or toluene, preferably acetonitrile.

It will be appreciated that definitions for rings A and B, $R_1$, W and X in compounds of formula (I-A), (I-B) and (I-C), or any embodiments thereof as described herein, correspond to those substituents, or protected forms thereof, as present in formula (I), or any embodiments thereof as described herein. Thus, in formulae (I-A) and (I-C), ring A is a monocyclic aryl or heteroaryl, optionally substituted with one or more substituents independently selected from halo, hydroxy, amino, nitro, carboxyl, carboxamido, cyano, —$SO_3H$, and optionally substituted $C_{1-8}$ alkyl, $C_{1-8}$ alkoxy, $C_{1-8}$ alkylamino or di($C_{1-8}$ alkyl)amino, wherein any one or more substituent on ring A may be unprotected or in a protected form; and in formula (I-B) W and X are, independently, hydrogen, halo, $C_{1-8}$ alkyl or $C_{1-8}$ alkoxy; ring B is a monocyclic aryl or heteroaryl, optionally substituted with one or more substituents independently selected from halo, hydroxy, amino, nitro, carboxyl, carboxamido, cyano, —$SO_3H$, and optionally substituted $C_{1-8}$ alkyl, $C_{1-8}$ alkoxy, 8 alkylamino or di($C_{1-8}$ alkyl)amino, wherein any one or more substituent on ring B may be unprotected or in a protected form; and $R_1$ is: (i) —$CH_2C(O)C(R_2)(R_3)$-L-$R_4$ or —$CH_2CHOHC(R_2)(R_3)$-L-$R_4$, in which: $R_2$ and $R_3$ are each, independently, H or $C_{1-3}$ aliphatic, halo, or $C_{1-3}$ haloaliphatic, or wherein $R_2$ and $R_3$ together with the intervening carbon atom to which they are bonded, form a $C_{3-6}$ carbocyclic moiety; L is a bond or $C_{1-3}$ alkylene; and $R_4$ is —$OR_5$ or —$SR_5$, wherein $R_5$ is hydrogen, optionally substituted alkyl (e.g. $C_{1-6}$ alkyl, such as methyl), a protecting group or —$C(O)R_6$, wherein $R_6$ is optionally substituted aliphatic, heteroaliphatic, aromatic or heteroaromatic moiety; (ii) —$CH_2CHOH(CH_2)_aR_7$ or —$CH_2C(O)(CH_2)_aR_8$ in which a is 0 or 1 and $R_7$ and $R_8$ are selected from alkyl and cycloalkyl groups and saturated heterocyclic groups optionally substituted at a hetero-atom; or (iii) an optionally substituted aliphatic moiety, wherein any one or more substituent on $R_1$ may be unprotected or in a protected form.

Any of the above embodiments of a process of the invention may, for example, be for producing a compound wherein at least one of ring A and ring B is unsubstituted or substituted phenyl or pyridyl. At least one of ring A and ring B may be unsubstituted, monosubstituted or disubstituted phenyl or unsubstituted, monosubstituted or disubstituted 2-, 3- or 4-pyridyl. Where ring A and/or ring B is substituted with optionally substituted $C_{1-8}$ alkyl, $C_{1-8}$ alkoxy, $C_{1-8}$ alkylamino or di($C_{1-8}$ alkyl)amino, the optional substituents on $C_{1-8}$ alkyl, $C_{1-8}$ alkoxy, $C_{1-8}$ alkylamino and di($C_{1-8}$ alkyl)amino include any substituent as described herein for substituents on an aliphatic group, for example, halo, —$NO_2$, —CN, amino, $C_{1-8}$ alkylamino, alkyl)amino, —S(O)H or —$CO_2H$. In some embodiments, ring A is phenyl having a meta substituent chosen from NHMe, NMeEt, $NEt_2$, F, Cl, Br, OH, $OCH_3$, $NH_2$, $NMe_2$, $NO_2$, Me, $(CH_2)_n$—$CO_2H$, CN, $CH_2NMe_2$, NHCHO and $(CH_2)_n$—$SO_3H$ where n is 0-2; unsubstituted phenyl or 2-, 3- or 4-pyridyl optionally with a substituent selected from F, Cl, $CH_3$ and $CO_2H$; and ring B is 2-, 3- or 4-pyridyl or phenyl. As described above, any one or more substituent on ring A or ring B may be unprotected or in a protected form.

In any of the above embodiments, W and X may independently be H, halo, $C_{1-3}$ alkyl or $C_{1-3}$ alkoxy. Preferably, W and X are both H.

Any of the above embodiments may, for example, be for producing a compound wherein $R_1$ is —$CH_2C(O)C(R_2)(R_3)$-L-$R_4$ or —$CH_2CHOHC(R_2)(R_3)$-L-$R_4$, preferably wherein $R_1$ is —$CH_2C(O)C(R_2)(R_3)$-L-$R_4$.

Alternatively, a process of the invention as described herein may be for producing a compound wherein $R_1$ is —$CH_2CHOH(CH_2)_aR_7$ or —$CH_2C(O)(CH_2)_aR_8$ in which a is 0 or 1 and $R_7$ and $R_8$ are, independently, alkyl, cycloalkyl or a saturated heterocyclic group optionally substituted at a hetero-atom. In some embodiments, $R_7$ and $R_8$ are selected from $C_{1-8}$ alkyl, $C_{3-8}$ cycloalkyl (which may be unsubstituted or substituted with one or more $C_{1-8}$ alkyl groups); and saturated heterocyclic groups of formulae (i-a) and (i-b):

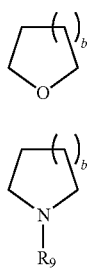

(i-a)

(i-b)

in which $R_9$ is H or $C_{1-3}$ alkyl or $C_{1-3}$ acyl and b is 1 or 2. In some embodiments, $R_7$ is $C_{4-7}$ linear or branched alkyl and $R_8$ is $C_{1-7}$ (preferably $C_{4-7}$) linear or branched alkyl.

In any of the above embodiments of the invention, a compound of formula (I-A) may be a compound of formula (II-A) as described below. In any of the above embodiments of the invention, a compound of formula (I-B) may be a compound of formula (II-B) as described below. In any of the above embodiments of the invention, a compound of formula (I-C) may be a compound of formula (II-C) as described below.

The compound of formula (I) may be a compound of formula (II):

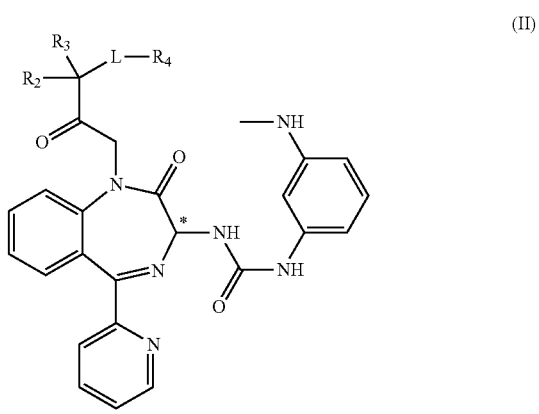

(II)

or a pharmaceutically acceptable salt thereof, wherein $R_2$, $R_3$, L and $R_4$ are as defined above in relation to formula (I). In an embodiment of the process of the invention where the compound of formula (I) is a compound of formula (II), the compound of formula (I-A) is a compound of formula (II-A), the compound of formula (I-B) is a compound of formula (II-B) and the compound of formula (I-C) is a compound of formula (II-C).

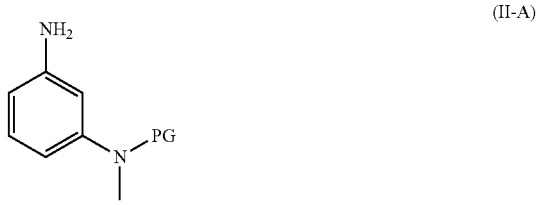

(II-A)

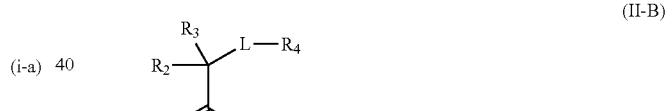

(II-B)

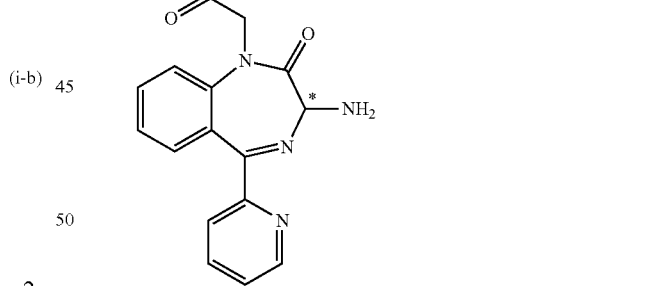

(II-C)

wherein PG is a protecting group, preferably a Boc protecting group. It will be appreciated that, in this embodiment or any of the further embodiments thereof as described herein, a protected form of compound (II):

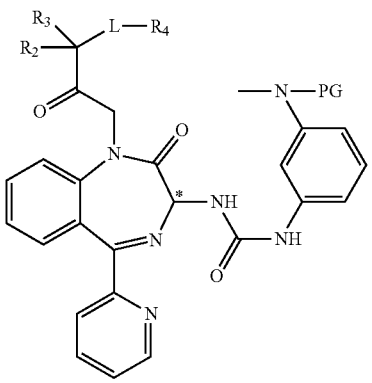

is initially formed in step (a) or (b) as described above and the process comprises the additional step of deprotection as described above to remove PG and form a compound of formula (II).

In any of the above embodiments, where $R_2$ and $R_3$ together with the intervening carbon atom to which they are bonded, form a carbocyclic moiety, the carbocyclic moiety may be a $C_{3-4}$ carbocyclic moiety.

In any of the above embodiments, $R_2$ and $R_3$ may each, independently, be H or $C_{1-2}$ alkyl and L may be a bond or $C_{1-3}$ alkylene. In some embodiments, $R_2$ and $R_3$ may each, independently, be $C_{1-2}$ alkyl and L may be $C_{1-3}$ alkylene. In some embodiments, $R_2$ and $R_3$ may each, independently, be H or $C_{1-2}$ alkyl and L may be $C_1$ alkylene (—CH$_2$—). In some embodiments, $R_2$ and $R_3$ may each, independently, be $C_{1-2}$ alkyl and L may be $C_1$ alkylene (—CH$_2$—).

In any of the above embodiments, where $R_1$ is —CH$_2$C(O)C($R_2$)($R_3$)-L-$R_4$ or —CH$_2$CHOHC($R_2$)($R_3$)-L-$R_4$ (preferably —CH$_2$COC($R_2$)($R_3$)-L-$R_4$), $R_4$ may be —OR$_5$ or —SR$_5$ wherein $R_5$ is hydrogen, methyl or —C(O)$R_6$, wherein $R_6$ is optionally substituted aliphatic, heteroaliphatic, aromatic or heteroaromatic moiety. In some embodiments, $R_6$ is optionally substituted aliphatic, for example $R_6$ is substituted or unsubstituted $C_{1-6}$ aliphatic, preferably substituted or unsubstituted $C_{1-3}$ aliphatic, more preferably methyl. Preferably, $R_4$ is —OR$_5$ and $R_5$ is —C(O)$R_6$.

The compounds of formula (I), (I-B), (II) and (II-B) contain a chiral centre at the position marked * and may exist in enantiomeric forms. Compounds may be provided as a racemic mixture of enantiomers, a non-racemic mixture of enantiomers or as a single enantiomer in optically pure form, for example the R-enantiomer at *:

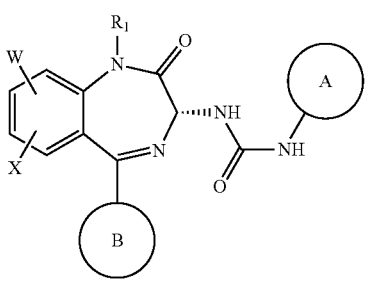

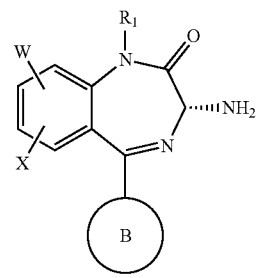

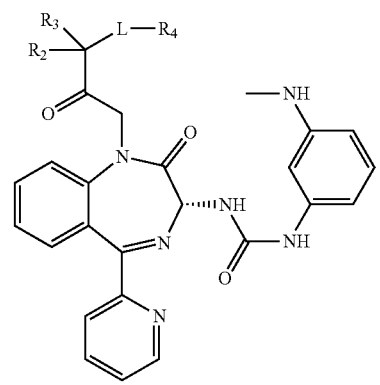

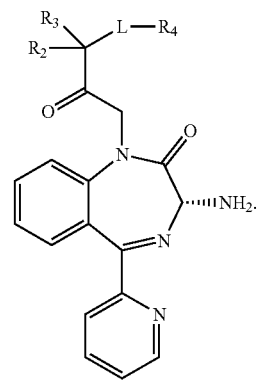

A compound of formula (I) or (II) may be, for example, a compound selected from:

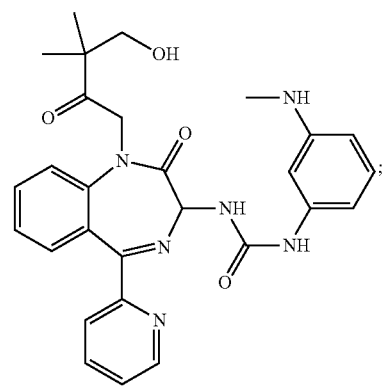

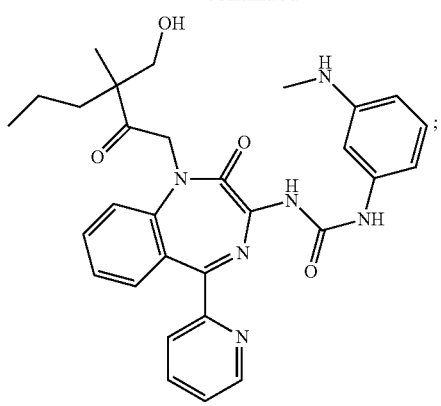
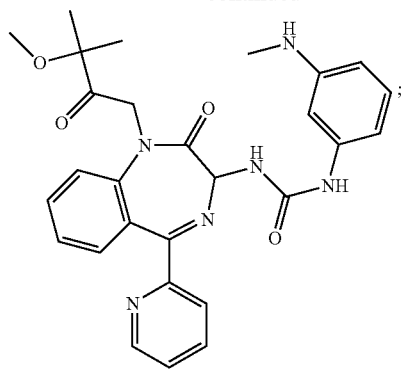
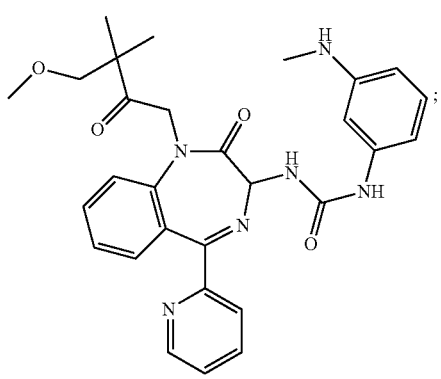
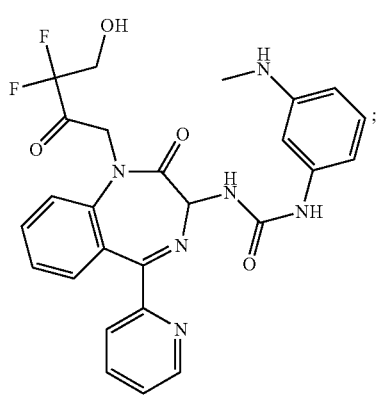
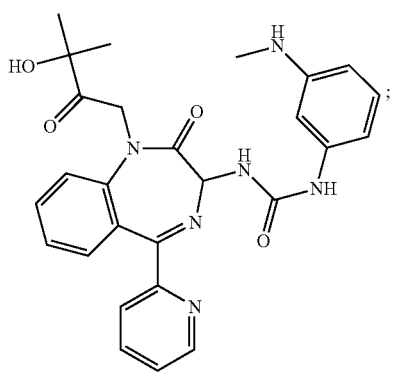
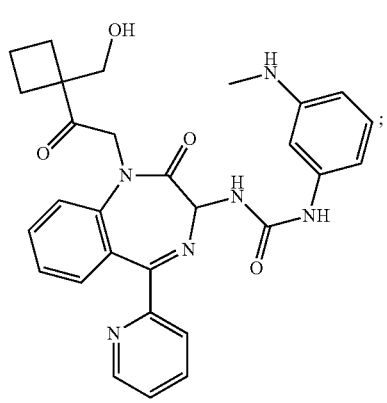
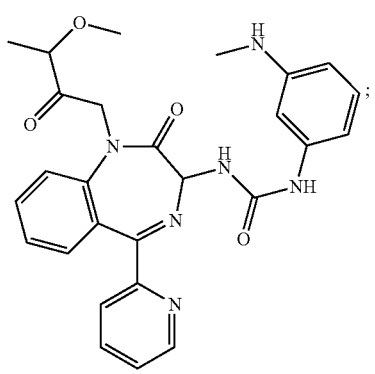
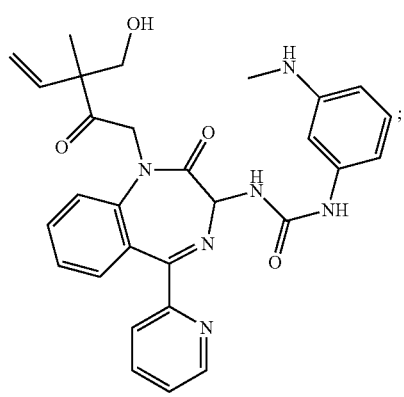

-continued
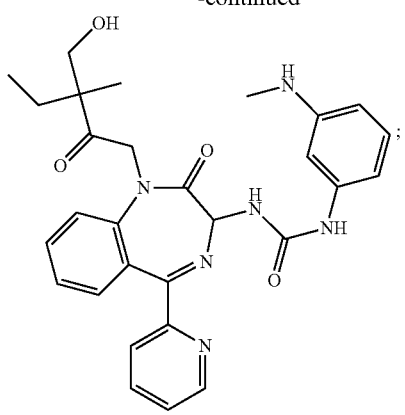
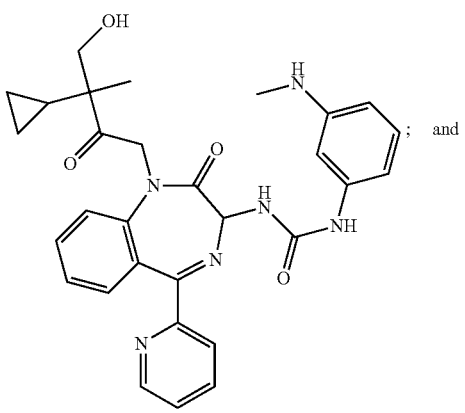
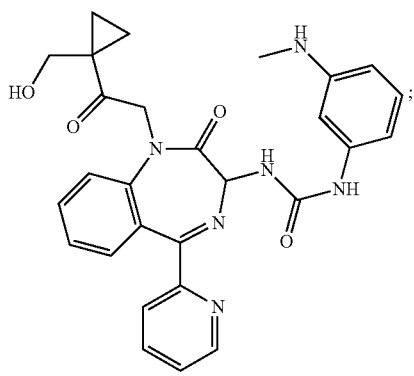
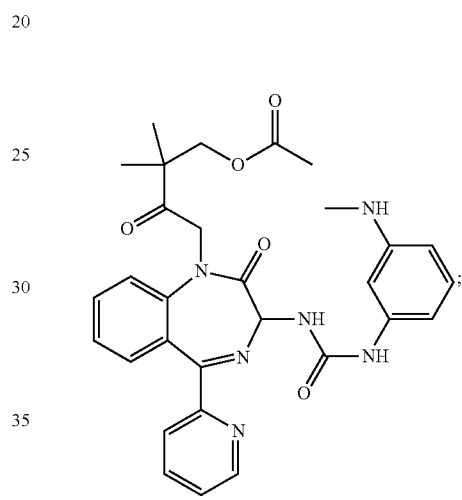
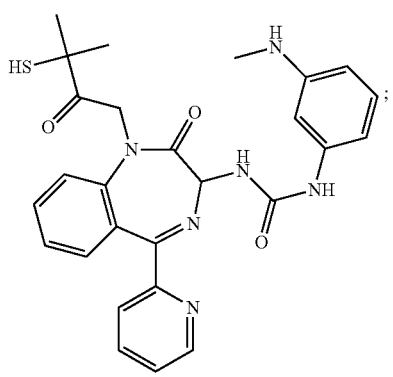
or a pharmaceutically acceptable salt thereof.
In some embodiments, the compound may be selected from:
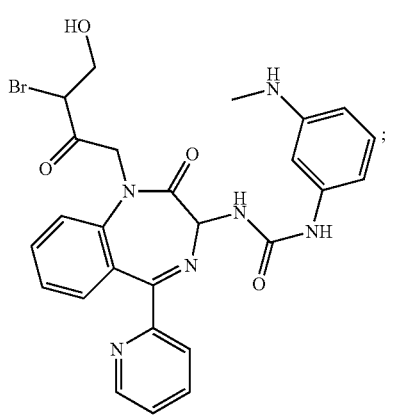
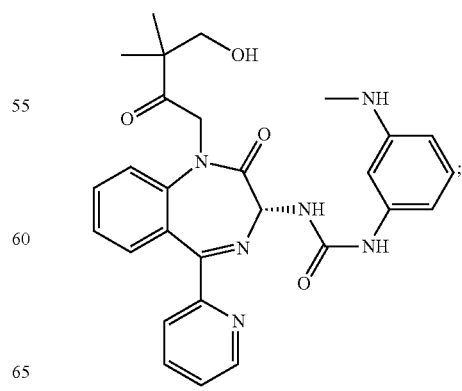

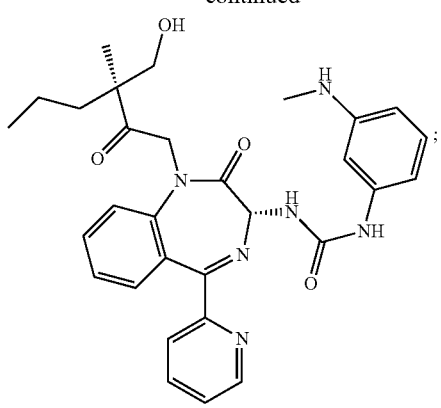
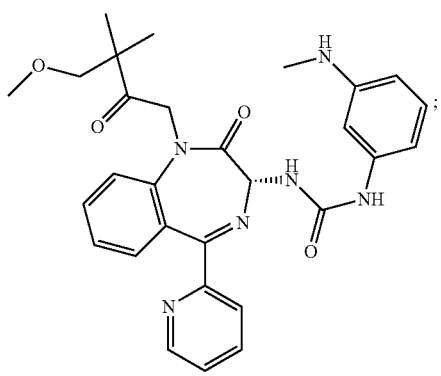
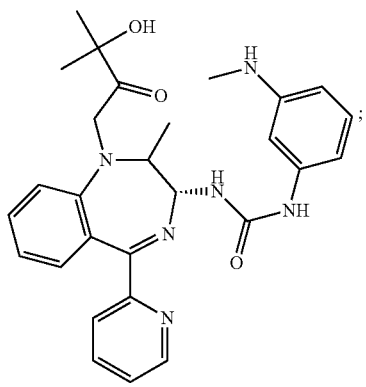
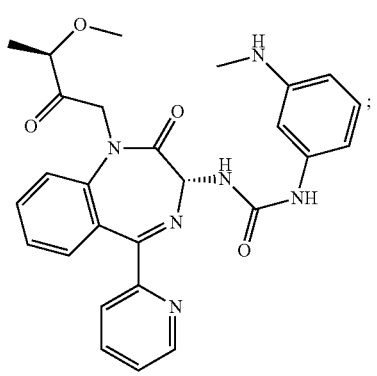
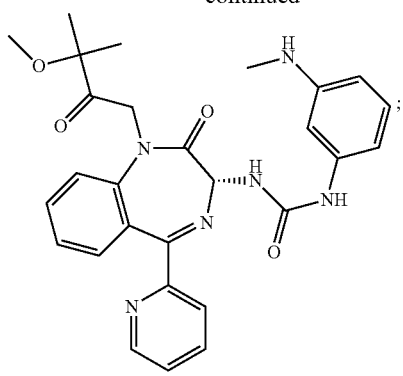
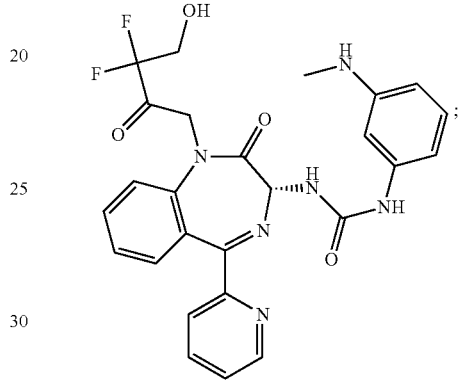
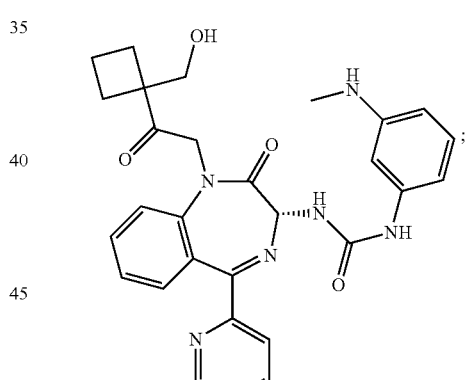
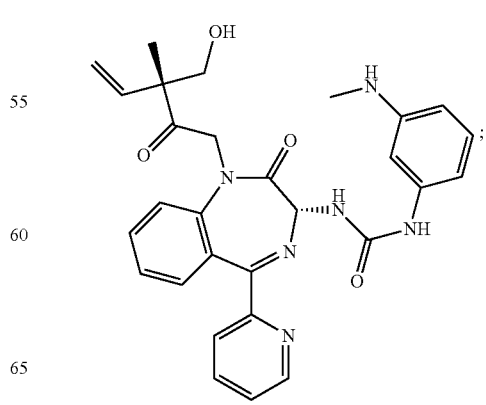

-continued
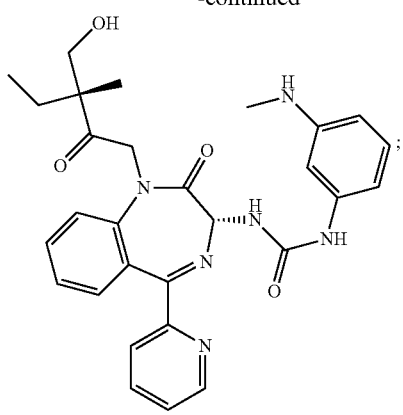
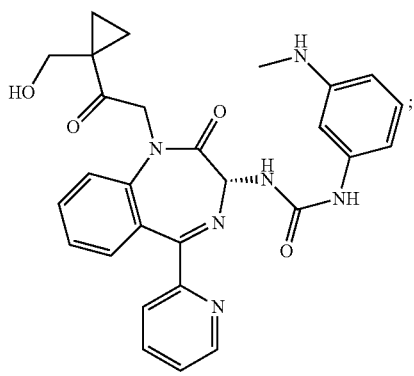
-continued
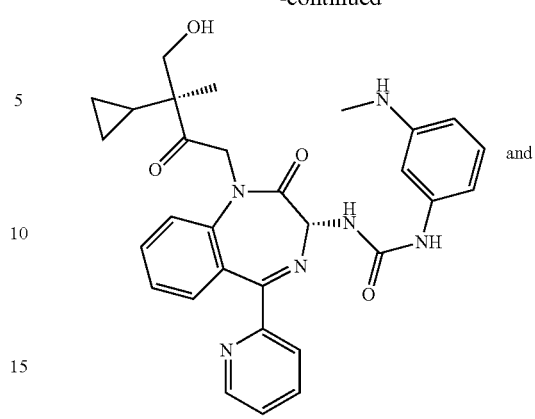
and
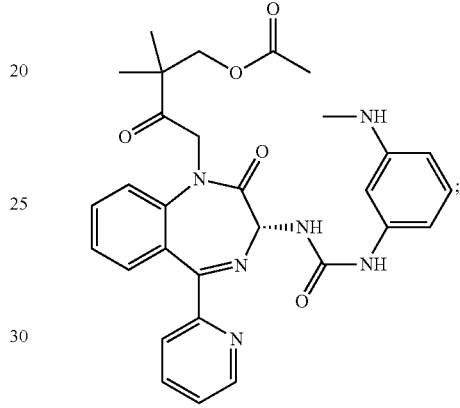
or a pharmaceutically acceptable salt thereof.
A compound of formula (II) may be a compound of formula (III):
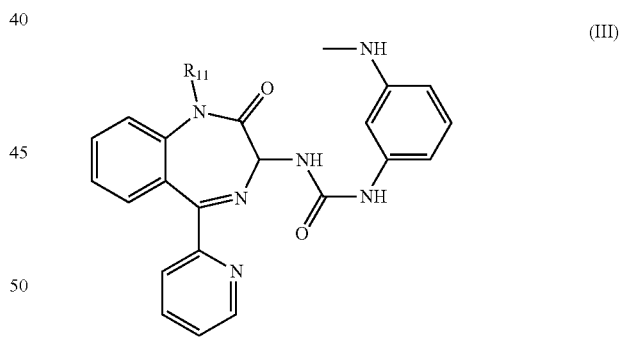
or a pharmaceutically acceptable salt thereof, wherein $R_{11}$ is selected from
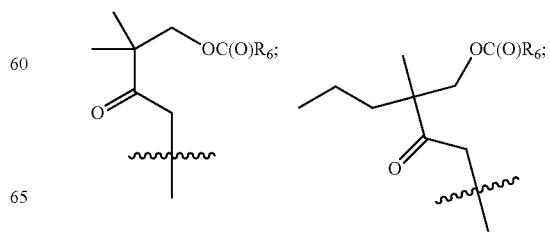

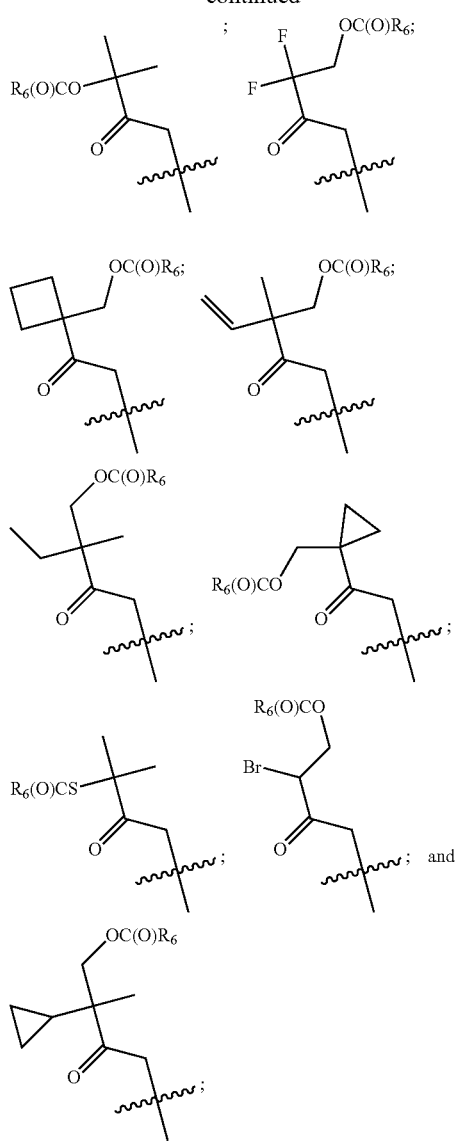
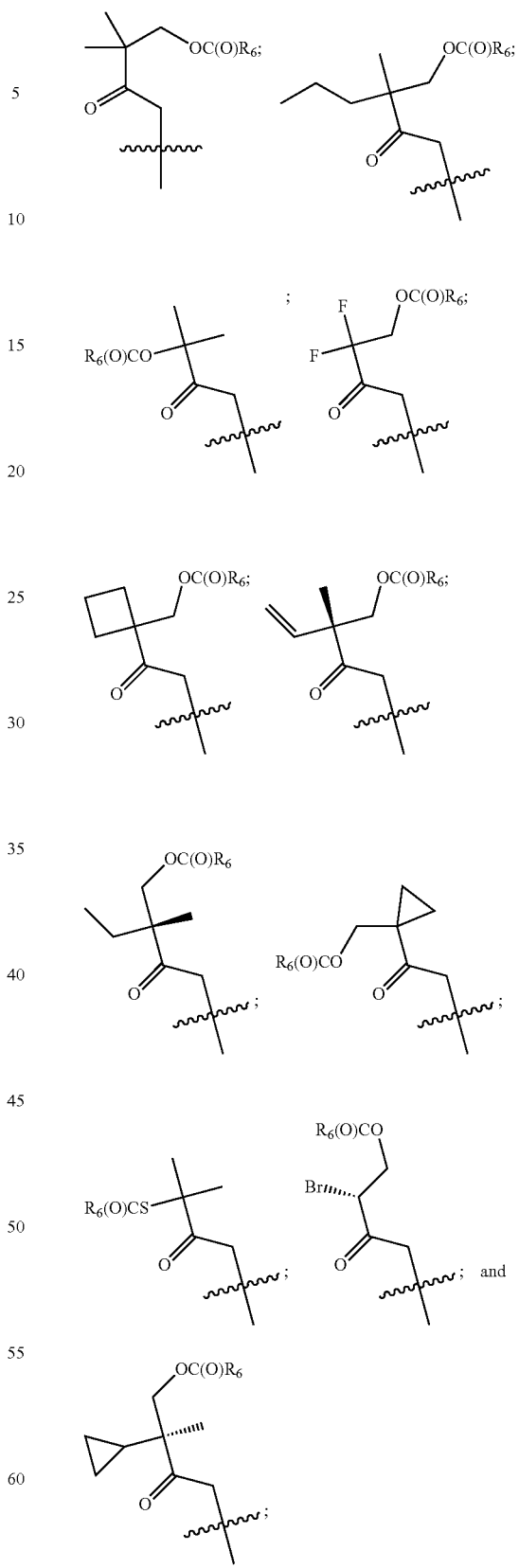
wherein $R_6$ is as defined for any of the embodiments of formula (I) or (II) above. In some embodiments, the compound may be a compound of formula (IV):
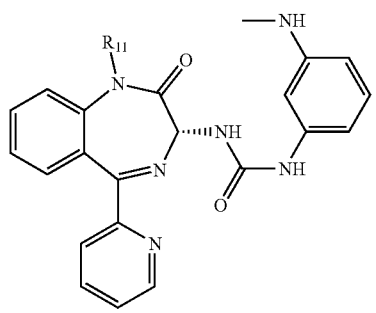
or a pharmaceutically acceptable salt thereof. Preferably, $R_{11}$ is selected from:
In a preferred embodiment, the compound of formula (I) or (II) is a compound (TR):

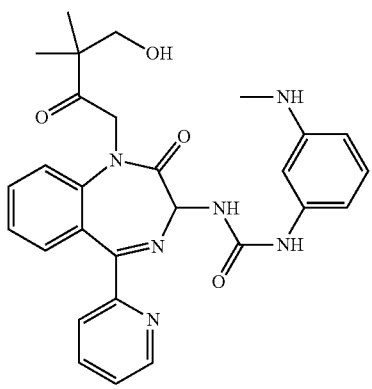
(TR)

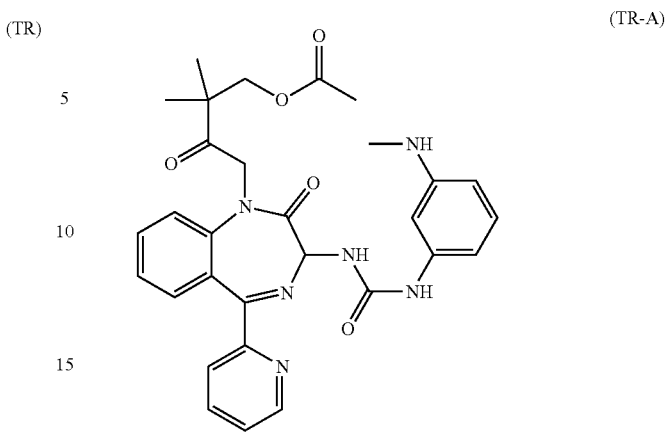
(TR-A)

or a pharmaceutically acceptable salt thereof. Compound (TR) contains a chiral centre and therefore exists as two enantiomers, designated (TR2) (the R-enantiomer) and (TR3) (the S-enantiomer).

or a pharmaceutically acceptable salt thereof. It will be appreciated that in this embodiment, the compound of (II-B) is a compound where —$CH_2C(O)C(R_2)(R_3)$-L-$R_4$ is —$CH_2C(O)C(Me)(Me)CH_2$—OC(O)Me. Thus, the compound of formula (I-A) may be a compound of formula (II-A) and the additional step of deprotection as described above may occur to remove PG and form a compound (TR-A). The compound (TR-A) may be provided as the racemic mixture (TR1-A) of the enantiomers (TR2-A) (the R-enantiomer) and (TR3-A) (the S-enantiomer), a non-racemic mixture of the enantiomers (TR2-A) and (TR3-A) or as a single enantiomer (TR2-A or TR3-A) in optically pure form.

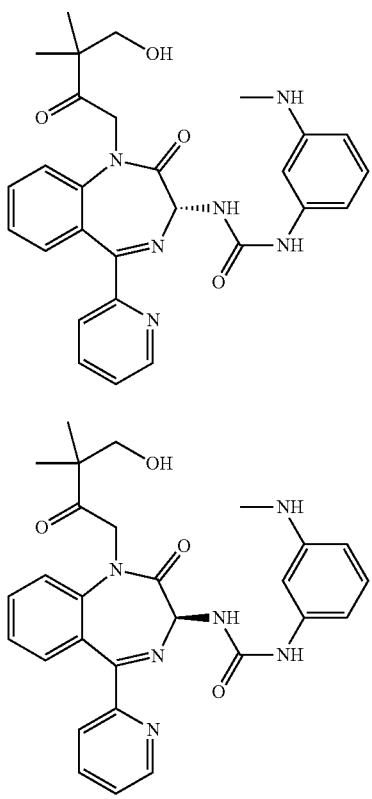
(TR2)

(TR3)

In a process of the invention, (TR) may be provided as the racemic mixture of the enantiomers (TR2) and (TR3), a non-racemic mixture of the enantiomers (TR2) and (TR3) or as a single enantiomer (TR2 or TR3) in optically pure form. The racemic mixture of (TR2) and (TR3) is designated "(TR1)" herein.

In a preferred embodiment, the compound of formula (I) or (II) is a compound (TR-A):

In another embodiment, the compound of formula (I) or (II) may be YF476:

YF476

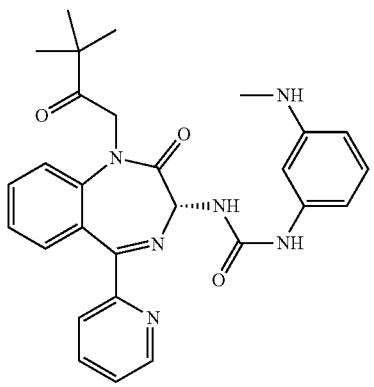

or a pharmaceutically acceptable salt thereof.

In an embodiment of the process of the invention, the process may be for producing a compound of formula (TR2-A):

(TR2-A)
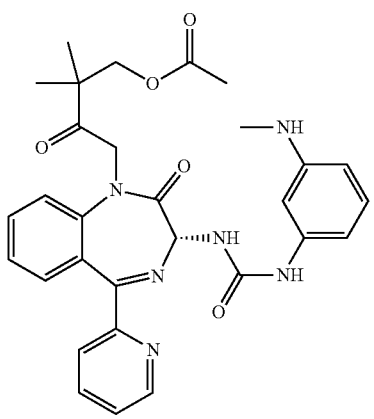

wherein the process comprises:

providing a reaction mixture by adding a compound of formula (II-A), a compound of formula (II-Ba) and a phosgene synthetic equivalent or phosgene to an aprotic solvent, to form a compound of formula (TR2-A) via initial formation of a compound of formula (TR2-A-PG)

(II-A)
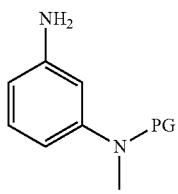

(II-Ba)
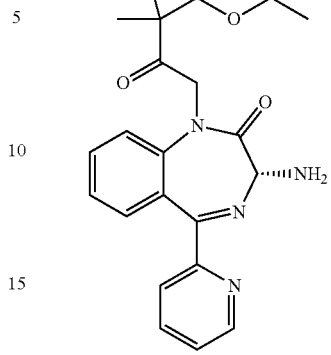

wherein PG is a protecting group, optionally a Boc protecting group; and (TR2-A-PG)
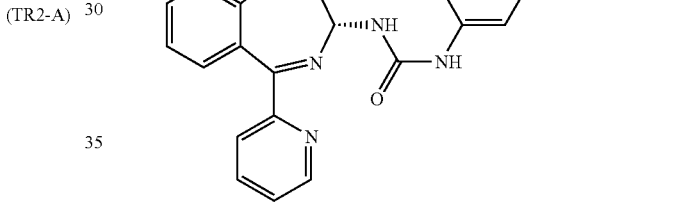

deprotecting the compound of formula (TR2-A-PG) to form a compound of formula (TR2-A).

The acetyl group of a compound of formula (TR2-A) may be removed to form a compound of formula (TR2).

A Boc protecting group may be deprotected under conditions known to a person of skill in the art, for example, by exposure to a strong acid such as TFA or HCl.

In an embodiment of the process of the invention, the process may be for producing a compound of formula (TR2):

(TR2)

wherein the process comprises:
providing a reaction mixture by adding a compound of formula (II-A), a compound of formula (II-Bb) and a phosgene synthetic equivalent or phosgene to an aprotic solvent, to form a compound of formula (TR2) via initial formation of a compound of formula (TR2-PG)

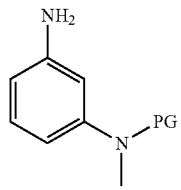
(II-A)

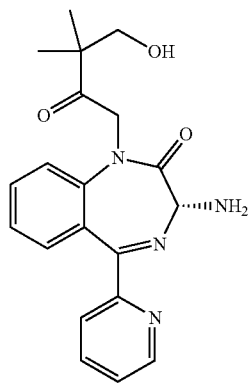
(II-Bb)

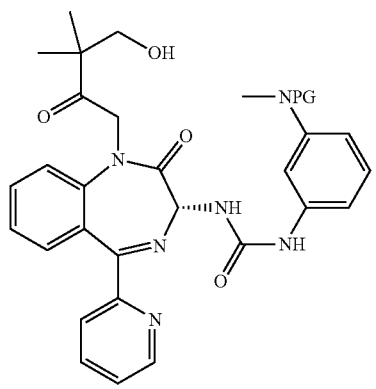
(TR2-PG)

wherein PG is a protecting group, optionally a Boc protecting group; and
deprotecting the compound of formula (TR2-PG) to form a compound of formula (TR2).

In a second aspect, the invention provides a compound obtained by a process according to the first aspect of the invention.

In a third aspect, the invention provides a compound of formula (II-C):

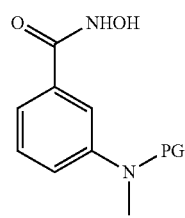
(II-C)

wherein PG is a protecting group, preferably a Boc protecting group.

An alternative process for producing a compound of formula (I), or a pharmaceutically acceptable salt thereof, comprises providing a reaction mixture by adding a compound of formula (V-A), a reagent or reagents capable of rearranging the compound of formula (V-A) to form a isocyanate intermediate of formula (V-B), and a compound of formula (I-B) to a non-aqueous solvent to form a compound of formula (I)

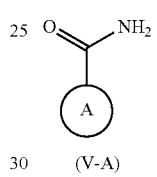
(V-A)

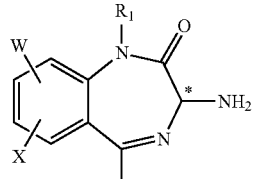
(V-B)

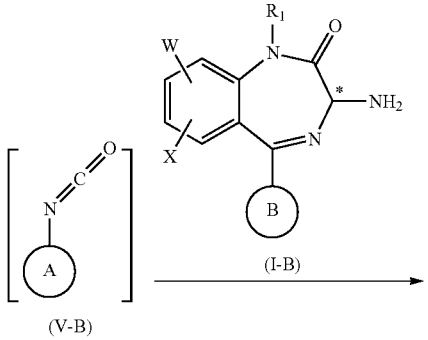
(I-B)

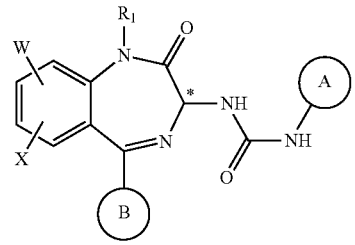
(I)

The reaction to form intermediate (V-B) may proceed via an N-bromo derivative (V-Bi)

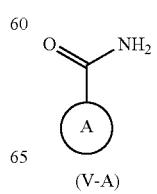
(V-A)

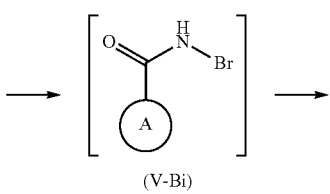
(V-Bi)

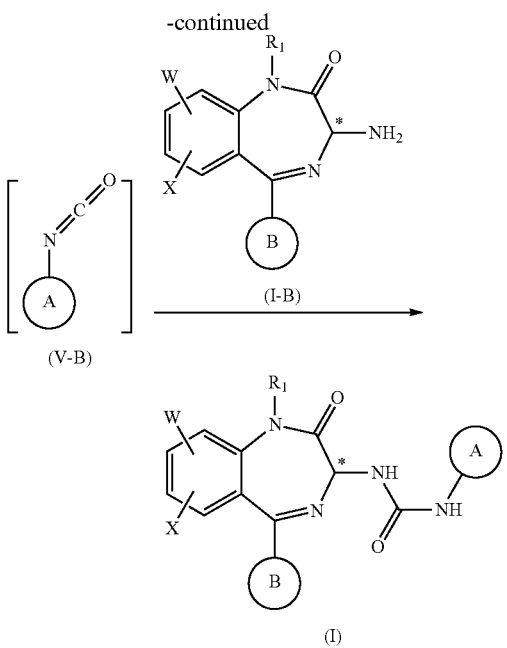

In this embodiment, the reagent or reagents capable of arranging the compound of formula (V-A) to form an isocyanate intermediate of formula (V-B) comprise a brominating agent, for example N-bromosuccinimide, and a base, for example DBU (1,8-diazabicyclo[5.4.0]undec-7-ene). The non-aqueous solvent may be an aprotic solvent, for example toluene, Intermediates (V-B) and (V-Bi) are formed and reacted with a compound of formula (I-B) in situ.

In the above process, the compounds of formula (I-B) and formula (I) and ring A of the compounds of formula (V-A), (V-B) and (V-Bi) are as defined above in any embodiment of the first aspect of the invention.

2-(2-Aminobenzoyl)pyridine may be utilised in the preparation of a compound of formula (II-B), or embodiments thereof, as described herein. 2-(2-aminobenzoyl)pyridine may be prepared by a process comprising reacting morpholine with isatoic anhydride to form N-(2-aminobenzoyl)morpholine and reacting N-(2-aminobenzoyl)morpholine with 2-lithiumpyridine to form 2-(2-aminobenzoyl)pyridine. 2-lithiumpyridine may be prepared by reacting 2-bromopyridine with n-butyl lithium. This process may be carried out in an aprotic solvent such as toluene.

DETAILED DESCRIPTION OF THE INVENTION

The meanings of terms used in the specification of the present application will be explained below, and the present invention will be described in detail.

The term "aliphatic", as used herein, means a substituted or unsubstituted straight-chain, branched or cyclic hydrocarbon, which is completely saturated or which contains one or more units of unsaturation, but which is not aromatic. Aliphatic groups include substituted or unsubstituted linear, branched or cyclic alkyl, alkenyl, alkynyl groups and hybrids thereof, such as (cycloalkyl)alkyl, (cycloalkenyl)alkyl or (cycloalkyl)alkenyl. In various embodiments, an aliphatic group has 1 to 12, 1 to 8, 1 to 6, or 1 to 3 carbons. For example, $C_{1-3}$ aliphatic encompasses straight chain and branched $C_{1-3}$ alkyl, alkenyl and alkynyl and cyclopropyl. The term "heteroaliphatic" means an aliphatic group in which one or more carbon atom is replaced by a heteroatom. The term "heteroatom" refers to nitrogen (N), oxygen (O), or sulfur (S).

The term "alkylene" refers to a bivalent alkyl group. An "alkylene" is a methylene or polymethylene group, i.e., —$(CH_2)_n$—, wherein n is a positive integer. An alkylene may be unsubstituted or substituted. A substituted alkylene is an alkylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "carbocyclic moeity" refers to a cyclic aliphatic group and includes, for example, cycloalkyl moieties.

The term "aryl" refers to a $C_{6-14}$ (preferably $C_{6-10}$) aromatic hydrocarbon, comprising one to three rings, each of which is optionally substituted. Aryl groups include, without limitation, phenyl, naphthyl, and anthracenyl. In some embodiments, two adjacent substituents on an aryl ring, taken together with the intervening ring atoms, form an optionally substituted fused 5- to 6-membered aromatic or 4- to 8-membered non-aromatic ring having 0-3 ring heteroatoms selected from the group consisting of N, O and S. Thus, the term "aryl", as used herein, includes groups in which an aromatic ring is fused to one or more heteroaromatic, cycloaliphatic, or heterocyclic rings, where the radical or point of attachment is on the aromatic ring.

The terms "heteroaryl" and "heteroar-" refer to an aromatic group having 5 to 14 ring atoms, preferably 5, 6, 9, or 10 ring atoms and having, in addition to carbon atoms, from one to four heteroatoms as ring atoms. The term "heteroatom" refers to N, O, or S. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of N, O and S. Thus, the terms "heteroaryl" and "heteroar-", as used herein, also include groups in which a heteroaromatic ring is fused to one or more aromatic, cycloaliphatic, or heterocyclic rings, where the radical or point of attachment is on the heteroaromatic ring.

As used herein, "halo" refers to fluoro, chloro, bromo or iodo.

As used herein, "haloaliphatic" refers to an aliphatic moiety as defined above, substituted by one or more halo moieties.

As used herein, "alkoxy" refers to a —O-alkyl moiety. The alkyl is as defined herein and, accordingly, may optionally be substituted as defined herein for optional substituents of an aliphatic moiety.

As used herein, "carboxamido" refers to a —C(O)NR$_2$ moiety, wherein each R is, independently, H or aliphatic, preferably H.

As used herein, the term "comprises" means "includes, but is not limited to."

The term "substituted", as used herein, means that a hydrogen radical of a designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites. Unless otherwise indicated, where multiple substituents are present, substituents may be either the same or different.

An aryl or heteroaryl group may be optionally substituted. Suitable substituents on the unsaturated carbon atom of an aryl or heteroaryl group include halo, —NO$_2$, —CN, —R', —C(R')=C(R')$_2$, —C≡C—R', —OR', —SR', —S(O)R', —SO$_2$R', —SO$_3$R', —SO$_2$N(R')$_2$, —N(R')$_2$, —NR'C(O)R', —NR'C(O)N(R')$_2$, —NR'CO$_2$R', —NR'SO$_2$R', —NR'SO$_2$N(R')$_2$, —O—C(O)R', —O—CO$_2$R', —OC(O)N(R'), —C(O)R', —CO$_2$R', —C(O)N(R')$_2$, —P(O)(R')$_2$, —P(O)(OR')$_2$, —O—P(O)—OR', wherein R', independently, is hydrogen or an optionally substituted aliphatic, heteroaliphatic, aromatic or heteroaromatic moiety, or two occurrences of R' are taken together with their intervening atom(s) to form an optionally substituted 5-7-membered aromatic, heteroaromatic, cycloaliphatic, or heterocyclic ring.

An aliphatic or heteroaliphatic group, including carbocyclic or heterocyclic rings, may be "optionally substituted". Unless otherwise defined, suitable substituents on the saturated carbon of an optionally substituted aliphatic or heteroaliphatic group, are selected from those listed above for the unsaturated carbon of an aryl or heteroaryl group and additionally include the following: =O, =S, =C(R")$_2$, where R" is hydrogen or an optionally substituted C$_{1-6}$ aliphatic group.

In addition to the substituents defined above, optional substituents on the nitrogen of a non-aromatic heterocyclic ring also include and are generally selected from R', —N(R')$_2$, —C(O)R', —C(O)OR', —S(O)$_2$R', —S(O)$_2$N(R')$_2$, wherein each a is defined above. A ring nitrogen atom of a heteroaryl or non-aromatic heterocyclic ring also may be oxidized to form the corresponding N-hydroxy or N-oxide compound.

As used herein, a "protected form" of a compound refers to a compound in which a functional moiety is protected by a protecting group. The functional moiety to be protected may be a hydroxyl, carboxyl, amino, or alkylamino moiety. Thus, a protected form as used herein may comprise a protected hydroxyl, protected carboxyl, or a protected amino or alkylamino moiety. Protection involves temporary blocking of the moiety so that a reaction can be carried out selectively at another reactive site in a multifunctional compound. A protected amino or alkyl amino may be protected by a protecting group, selected from protecting groups including, but not limited to, carbamates (including methyl, ethyl and substituted ethyl carbamates (e.g., Troc), carbobenzyloxy (Cbz), tert-butyloxycarbonyl (Boc), 9-fluorenylmethyloxycarbonyl (Fmoc), p-methoxybenzyloxycarbonyl (Moz or MeOZ), acetyl (Ac), benzoyl (Bz), benzyl (Bn), p-methoxybenzyl (PMB) 3,4-dimethoxybenzyl (DMPM), p-methoxyphenyl (PMP), succinyl (Suc), methoxysuccinyl (MeOSuc), formyl, urethane protecting groups, tosyl (Ts), other sulfonamides (e.g. Nosyl & Nps). For example, in certain embodiments, as detailed herein, certain exemplary oxygen protecting groups are utilized. A protected hydroxyl or carboxyl may be protected by an oxygen protecting group, selected from protecting groups including, but not limited to, acetyl (Ac), benzoyl (Bz), benzyl (Bn), pivaloyl (Piv), methyl ethers, substituted methyl ethers (e.g., MOM (methoxymethyl ether), β-methoxyethoxymethyl ether (MEM), MTM (methylthiomethyl ether), BOM (benzyloxymethyl ether), p-methoxybenzyl (PMB), PMBM (p-methoxybenzyloxymethyl ether), substituted ethyl ethers, ethoxyethyl ethers, substituted benzyl ethers, methoxytrityl (MMT), tetrahydropyranyl (THP), trityl (Tr), silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether, TOM (tri-iso-propylsilyloxymethyl)), esters (e.g., formate, acetate (Ac), benzoate (Bz), trifluoroacetate, dichloroacetate), carbonates, cyclic acetals and ketals. It will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

An "aprotic solvent" is used herein in accordance with standard terminology in the art to refer to a solvent which is incapable of acting as a proton donor. Aprotic solvents include, but are not limited to, dichloromethane, tetrahydrofuran, ethyl acetate, acetonitrile, dimethylformamide, dimethyl sulfoxide, acetone, hexane, pentane, benzene, toluene, 1,4-dioxane, diethyl ether, and chloroform.

A "protic solvent" is used herein in accordance with standard terminology in the art to refer to a solvent which is capable of acting as a proton donor. Generally, such a solvent has has a labile hydrogen atom bound to an oxygen or a nitrogen. Protic solvents include, but are not limited to, water, alcohols (e.g. methanol, ethanol, isopropyl alcohol), acetic acid, formic acid, hydrogen fluoride, and ammonia.

A "phosgene synthetic equivalent" used in a process of the invention may, for example, be carbonyldiimidazole, diphosgene, triphosgene, a chloroformate e.g 4-nitrophenyl chloroformate or disuccinimidyl carbonate (DSC).

A chloroformate is a compound of formula ClC(O)OR. R may be, for example, optionally substituted aliphatic, heteroaliphatic, aryl or heteroaryl.

Compounds of formula (I) and (II) as described herein may be of use as CCK$_2$/gastrin receptor antagonists and may be useful for the prevention and/or treatment of disorders associated with CCK$_2$/gastrin receptors, disorders caused by or associated with hypergastrinaemia and gastric acid-related disorders. Such disorders include disorders associated with CCK$_2$ receptor-bearing cells or failure or dysfunction of a physiological function in which gastrin is involved. Accordingly, examples of disorders that can be treated and/or prevented include, without limitation, any one or more of gastric and duodenal ulcers, non-steroid anti-inflammatory drug (NSAID)-induced gastric ulceration, dyspepsia, gastro-oesophageal reflux disease (GORD), Barrett's oesophagus, Zollinger-Ellison syndrome (ZES), hypergastrinaemia induced by a proton pump inhibitor (PPI) or other acid-suppressant (including the effects of withdrawal) and conditions caused by hypergastrinaemia (such as bone loss, impaired bone quality and bone fractures), gastritis (including *H. pylori*-induced gastritis and complications of autoimmune chronic atrophic gastritis, such as gastric carcinoids and enterochromaffin-like (ECL)-cell hyperplasia), neuroendocrine tumours (not limited to gastric carcinoids), parietal cell hyperplasia, fundic gland polyps, gastric cancer, colorectal cancer, medullary thyroid cancer, pancreatic cancer, and small cell lung cancer. The compounds may also be useful for the prevention and/or treatment of disorders induced by the dysfunction of a physiological function controlled by the central or peripheral CCK$_2$ receptor, for example anxiety, nociception, pain, drug addiction, analgesic dependence and analgesia withdrawal reactions.

Compounds of formula (I) and (I-B), and embodiments thereof as described herein, have at least one chiral carbon atom and may have more than one chiral carbon atom. The invention includes any enantiomeric form, at any level of optical purity, and mixtures thereof, both racemic and non-racemic. Accordingly, all stereoisomeric forms of the compounds disclosed herein form part of the invention. An optically pure form of an enantiomer as referred to herein has an enantiomeric excess (ee) of at least 90%, preferably at least 95%, more preferably at least 98%, and even more preferably at least 99%. ee may be assessed, for example, by chiral HPLC.

The compounds disclosed herein can exist in unsolvated as well as solvated forms for example with pharmaceutically acceptable solvents such as water, ethanol, and the like, and it is intended that the invention embrace both solvated and unsolvated forms. The compounds as described herein, their enantiomers and mixtures thereof, may be provided as the free compound or as a suitable salt or hydrate thereof. Salts should preferably be those that are pharmaceutically acceptable, and salts and hydrates can be prepared by conventional methods, such as contacting a compound of the invention with an acid or base whose counterpart ion does not interfere with the intended use of the compound. Examples of pharmaceutically acceptable salts include hydrohalogenates, inorganic acid salts, organic carboxylic acid salts, organic sulphonic acid salts, amino acid salt, quaternary ammonium salts, alkaline metal salts, alkaline earth metal salts and the like. Basic compounds may form non-toxic acid addition salts with various inorganic and organic acids, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, toluenesulfonate and pamoate salts. Acidic compounds may form salts with various pharmacologically acceptable cations, including alkali metal or alkaline earth metal salts, particularly calcium, magnesium, sodium, lithium, zinc, potassium, and iron salts. Compounds that include a basic or acidic moiety may also form pharmaceutically acceptable salts with various amino acids.

EXAMPLES

Abbreviations

DCM dichloromethane
DIPEA N,N'-diisopropylethyl amine
DMF N,N'-dimethylformamide
DMS dimethyl sulphate
GC gas chromatography
HPLC high performance liquid chromatography
MeI methyliodide
MTBE methyltert-butylether
THF tetrahydrofuran
TLC thin layer chromatography
UV ultra violet Gas chromatography was carried out on a Shimadzu GC2014. HPLC was carried out on an Agilent/HP 1100 reverse phase HPLC system. NMR spectra were recorded on a 400 Mz Bruker Avance 111 spectrometer with QNP (1H/13C/19F/31P/Cryoprobe) or 500 Mz Bruker Avance 111 HD spectrometer with dual (1H/13C). Elemental analysis (CHN) was performed on an Exeter Analytical CE-440 elemental analyser. XPRD spectra were obtained on a Pananalytical X'pert Pro diffractometer.

The following examples of the invention are provided to aid understanding of the invention but should not be taken to limit the scope of the invention. Unless otherwise described, reagents may be commercially available or prepared according to procedures in the literature.

Reference Example—Process with Use of Azide Chemistry

The process of the invention avoids the need for potentially explosive azide chemistry. Solely for reference purposes, a reaction scheme, in parts A and B, showing the use of azide chemistry as avoided by a process of the invention is provided below.

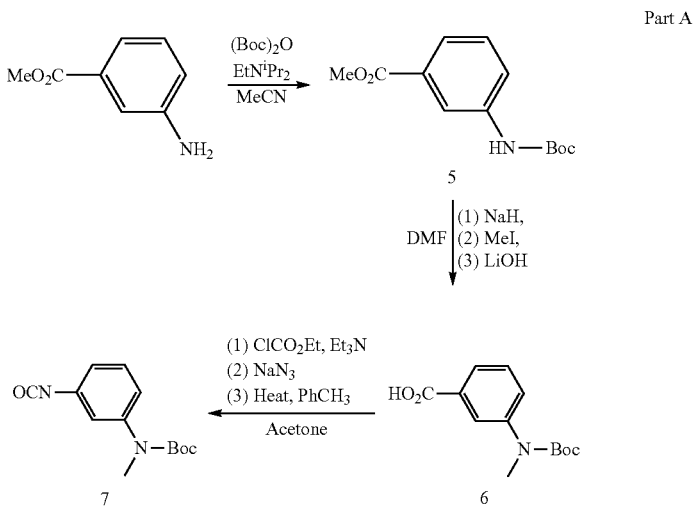

Part A

-continued
Part B
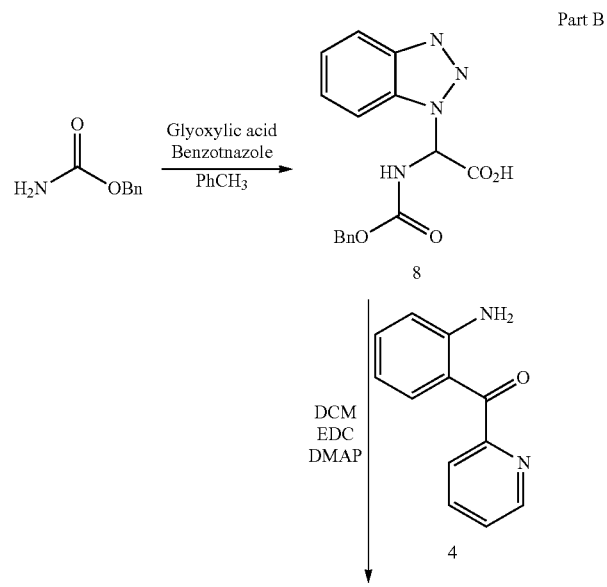
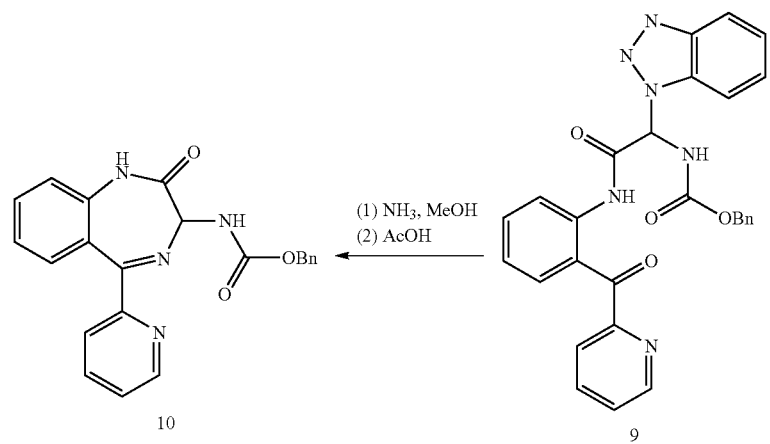
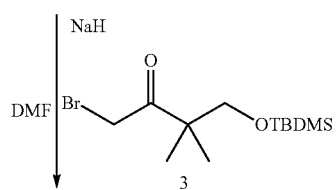

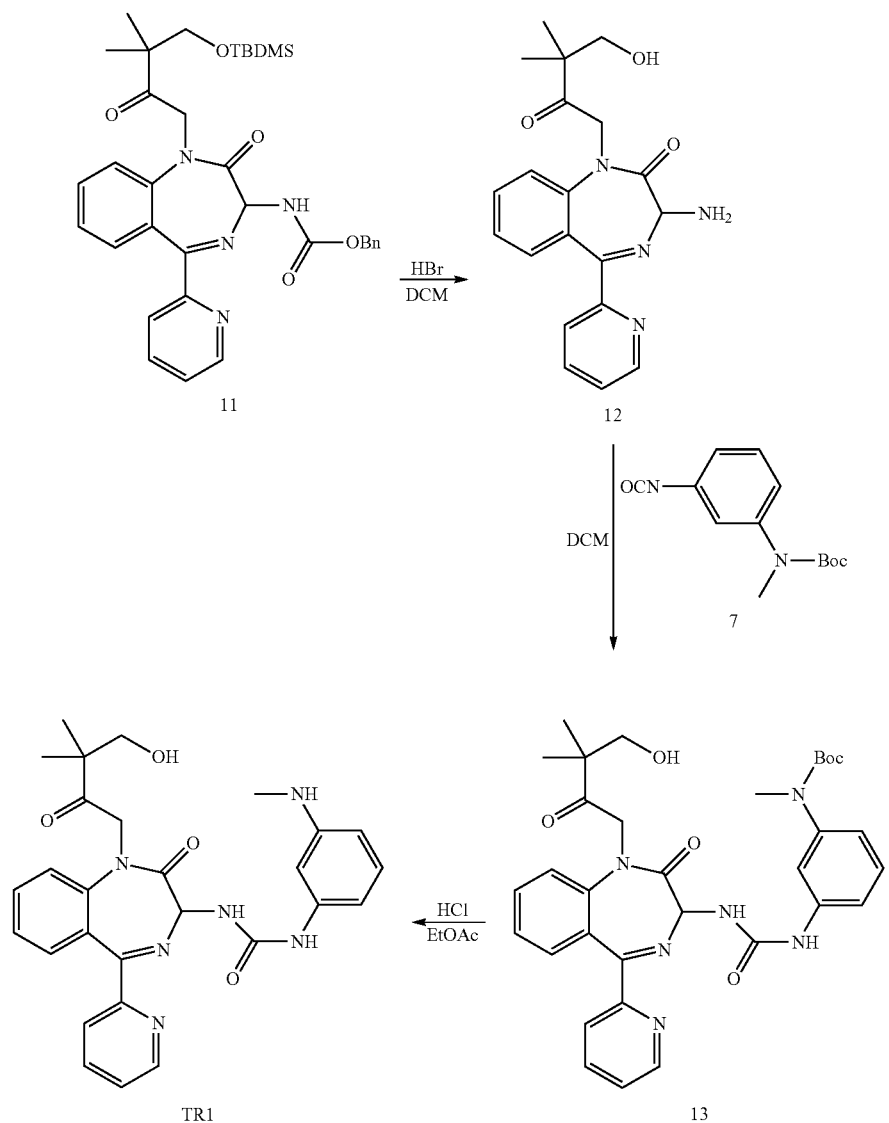

Racemic mixture (TR1) may, if desired, be resolved by chiral HPLC chromatography, for example with column: Chiralcel OD 250 mm×20 mm, 5 μm; mode: super critical fluid (SFC); eluent: Methanol 40%, no modifier; flow: 50 mL/min and run time: 4 min.

Example 1: Synthesis of (TR2) and (TR2-A) Via tert-Butyl (3-aminophenyl)methylaminocarbamate (N4)

(TR2) and (TR2-A) were synthesised according to the Scheme 1 below. It will be appreciated that this scheme can be applied generally to the synthesis of compounds of formula (I) by variation of the starting materials N4 and 14-A, as appropriate.

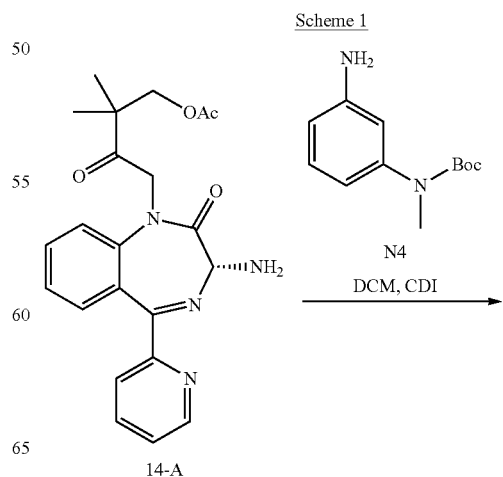

Scheme 1

-continued
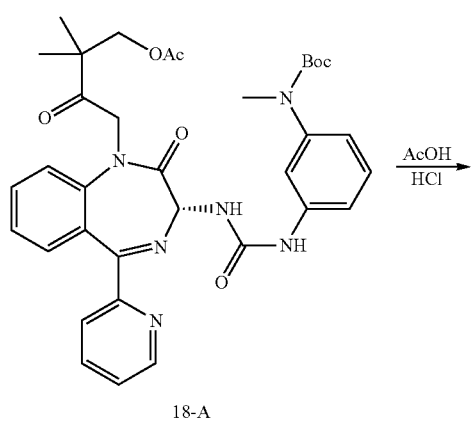
18-A
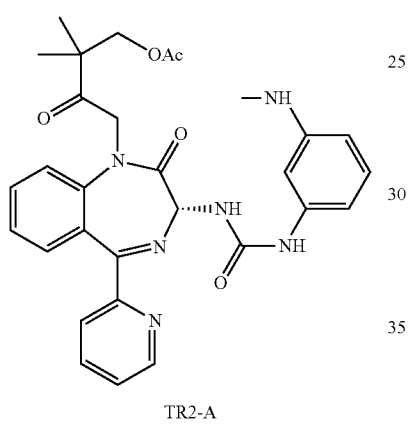
TR2-A
↓ K₂CO₃  
MeOH, H₂O
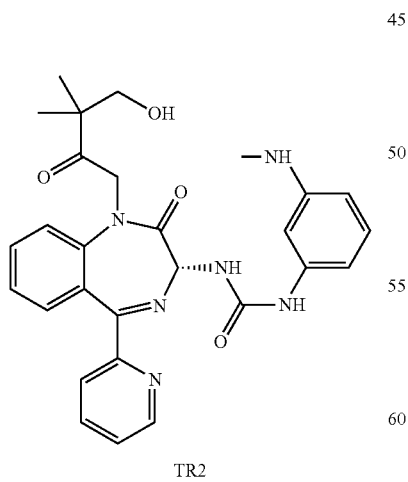
TR2
Compound 14-A was synthesised according to Scheme 2 below:
Scheme 2
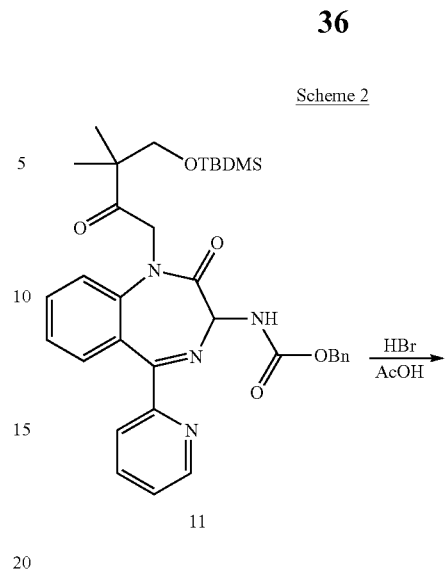
11
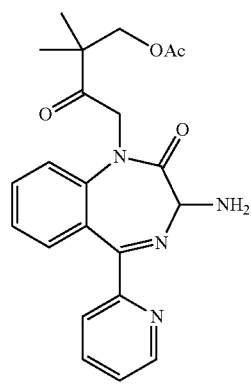
13-A
Chiral resolution using R-Mandelic acid | MeCN
↓
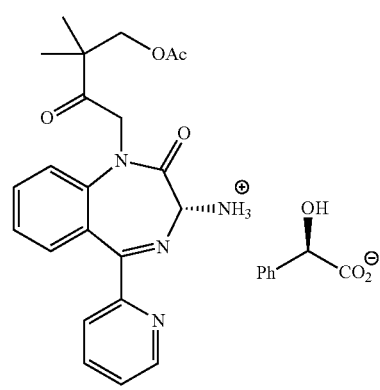
14-A R-Mandelate salt
DCM, H₂O | NaHCO₃
↓

37
-continued
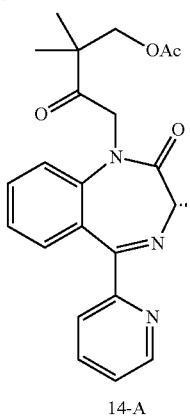
14-A
Scheme 3
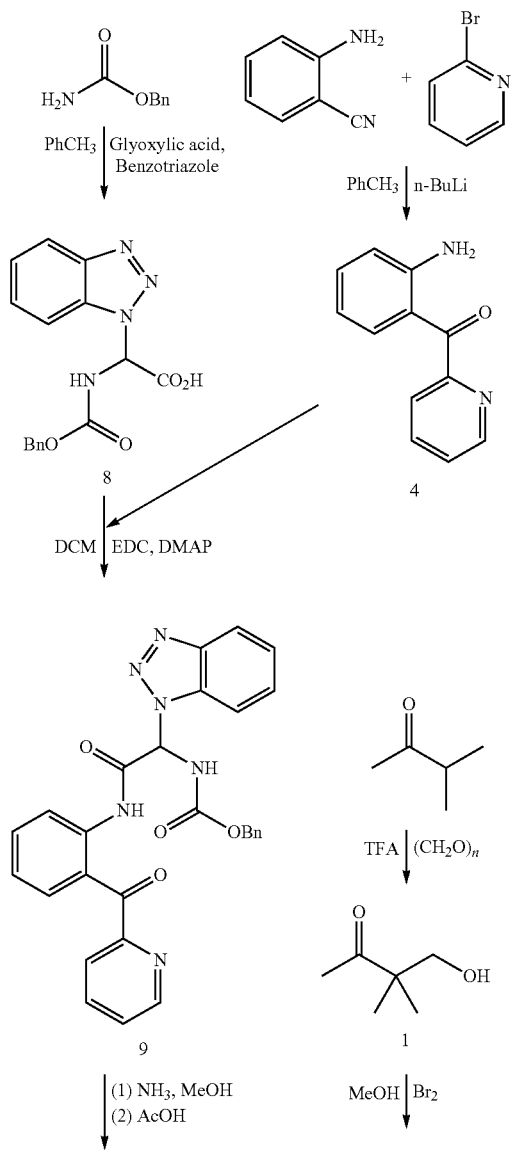
38
-continued
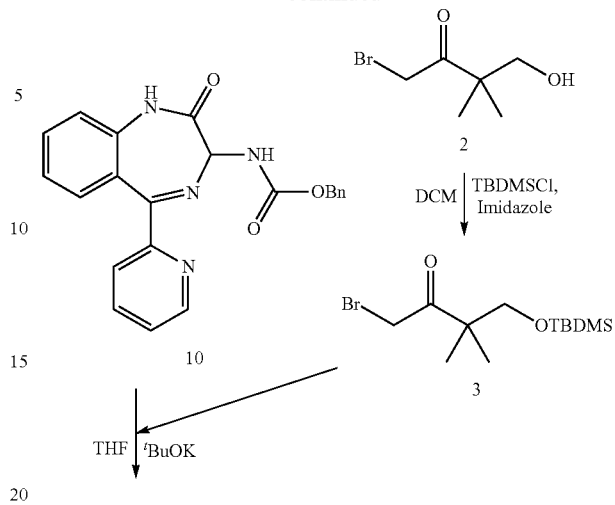
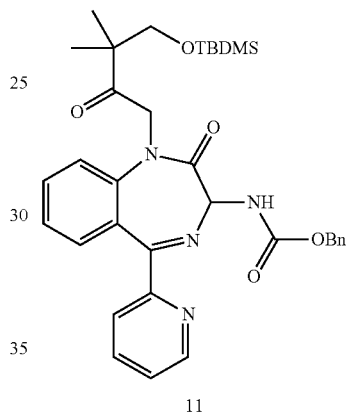
Compound N4 was synthesised according to Scheme 4 below:
Scheme 4
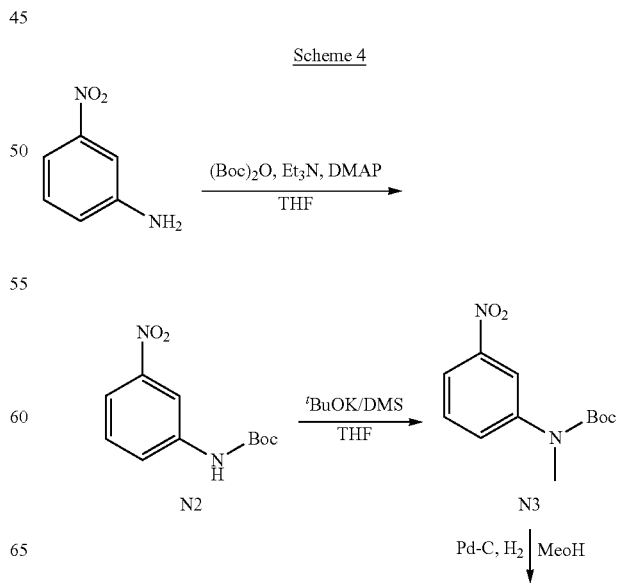

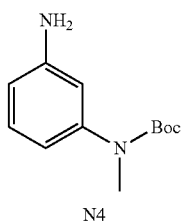

Scheme 4 illustrates synthesis of N4 via N2 and N3. Whilst exemplary reagents are illustrated in Scheme 4, it will be appreciated that these may be varied. For example, Boc in N2 to N4 may be replaced with an alternative amino protecting group, such as Fmoc, Cbz or Ac. Conversion of 3-nitroaniline to N2 could, for example, use organic bases other than triethylamine, e.g. DIPEA. The methylation of N2 to N3, preferably involves use of a base (e.g. KO′Bu or NaH) and a methylating agent (e.g. DMS or MeI). The solvent in this step may be an aprotic solvent, preferably a polar aprotic solvent (e.g. DMF or THF). Reduction of N3 to N4 could be performed with iron metal or by hydrogenation on a catalyst such as palladium on carbon or Raney Nickel.

4-Hydroxy-3,3-dimethyl-2-butanone (1)

Paraformaldehyde (465 g, 15.48 mol) and 3-methyl-2-butanone (1111 g, 12.90 mol) were added to trifluoroacetic acid (6.0 L) and the mixture slowly warmed to 90° C. in an oil bath over a one hour period. All the paraformaldehyde dissolved at about 50° C. The oil bath was cooled to 75° C. (cardice addition to the oil). Once the flask content temperature reduced to 85° C. a further charge of paraformaldehyde (465 g, 15.48 mol) and 3-methyl-2-butanone (1111 g, 12.90 mol) was added. The mixture slowly exothermed to about 92° C. (the oil bath was still at 75° C.). Once the flask content temperature had reduced to 85° C. the final charge of paraformaldehyde (465 g, 15.48 mol) and 3-methyl-2-butanone (1111 g, 12.90 mol) was added. After the exotherm was over, the mixture was stirred at 90° C. for a further 8 hours before cooling back to room temperature overnight. GC (of a small sample added to water and adjusted to pH=14 with sodium hydroxide then extracted into DCM) indicated about 2% 3-methyl-2-butanone and 86% product. The product solution was poured into a stirred mixture of ice (16 kg; extra cold from freezer) and solid sodium hydroxide (3 kg). A further charge of sodium hydroxide (about 260 g) was added to just bring the pH to 14. GC indicated hydrolysis was complete. The aqueous solution was saturated with sodium chloride (about 3 kg added) then without delay extracted with DCM (3×8 L). The combined DCM layers were washed with saturated brine (3 L) and dried over anhydrous sodium sulfate. The solution was evaporated under vacuum to give a light brown liquid (about 3.7 kg). The crude product was distilled through a 20 cm Vigreux distillation column at about 95° C./45 mmHg (A fore cut was removed and some residue remained after distillation) to give a near colourless product (2.85 kg, 63% yield, GC purity=98%).

1-Bromo-4-hydroxy-3,3-dimethyl-2-butanone (2)

Compound 1 (2566 g, 22.09 mol) was dissolved in methanol (13 L) and stirred at 20° C. The reaction flask was covered to protect it from light. Bromine (200 g, 1.25 mol) was added over 15 minutes. After a short induction period the reaction decolourised and a slight exotherm occurred. Once the mixture had decolourised it was cooled to 0° to 5° C. Bromine (3300 g, 20.65 mol) was slowly added over a two hour period while maintaining the temperature at 0°-5° C. (decolourisation was now fast). GC indicated about 94% product and <1% starting material. Several small after-peaks could also be seen by GC. Without delay the mixture was poured into saturated brine solution (20 L) and ice (4 kg) then extracted with DCM (4×8 L). The combined DCM extracts were washed with saturated brine (2×5 L) and then dried over anhydrous sodium sulfate. The solution was evaporated under vacuum at 40° C. to give a light yellow/brown liquid (4191 g, 97% yield, GC purity 91%).

1-Bromo-4-(tert-butyl-dimethyl-silanyloxy)-3,3-dimethyl-2-butanone (3)

Imidazole (645 g, 9.47 mol) was added to DCM (8.5 L) and cooled to −15° C. to −20° C. under a nitrogen atmosphere. Compound 2 (1650 g, 8.46 mol) was added to give a clear solution at −15° C. to −20° C. tert-Butyl-dimethyl-silyl chloride (1365 g, 9.06 mol) was slowly added while maintaining the temperature at −15° C. to −20° C. The mixture was stirred for a further 3 hours at that temperature. GC indicated 78% product, less than 1% starter and 14% residual tert-butyl-dimethylsilyl chloride. The reaction mixture was poured into cold water (7.5 L). The aqueous layer was removed and re-extracted with more DCM (2 L). The combined DCM layers were washed with water (2×2 L) then with saturated brine (2×3 L) before drying over anhydrous sodium sulfate. The solution was evaporated under vacuum at 40° C. to give a yellow oil (2559 g, 97% yield, GC purity about 75%).

$^1$H NMR (400 MHz, CDCl$_3$) δ 4.24 (s, 2H); 3.55 (s, 2H); 1.17 (s, 6H); 0.86 (s, 9H); 0.02 (s, 6H).

2-(2-Aminobenzoyl)pyridine (4)

2-bromopyridine (1075 g, 6.80 mol) in toluene (4.2 L) was cooled to <−65° C. while stirring under a nitrogen atmosphere. n-Butyl lithium (1.6 M in hexane; 4160 mL, 6.66 mol) was added over a one hour period while maintaining the temperature <−60° C. The mixture was stirred at <−60° C. for 30 minutes before checking for the absence of 2-bromopyridine by GC. A solution of 2-aminobenzonitrile (350 g, 2.96 mol) in toluene (2.3 L) (may need warming slightly to dissolve) was slowly added over a 30-minute period while maintaining the temperature at <−60° C. The mixture was allowed to warm slowly to room temperature while stirring overnight. The mixture was carefully poured into cold hydrochloric acid solution (1.96 L 32% hydrochloric acid, 3 L water and 2 kg ice) while stirring. The mixture was stirred for a further hour before allowing the layers to separate. The lower aqueous layer was removed and the upper organic layer was extracted with hydrochloric acid solution (350 mL of 32% hydrochloric acid and 3 L of water). Ice (4 kg) was added to the combined acidic aqueous layers before adjusting to pH=10 with 35% ammonia solution (about 6.5 L). Add more ice as required to achieve a final temperature of 0-5° C. The slurry was stirred at 0-5° C. for a further 30 minutes. The slurry was filtered and washed with water until free of ammonia. The product was dried in a circulated air oven at 50° C. (until a constant weight was achieved) to give a yellow/orange solid (558 g, 95% yield, 87% GC purity).

2-(Benzotriazol-1-yl)-2-(benzyloxycarbonylamino)-acetic acid (8)

A vigorously stirred mixture of benzotriazole (512 g, 4.30 mol), benzyl carbamate (650 g, 4.30 mol) and glyoxylic acid monohydrate (396 g, 4.30 mol) in toluene (12 L) was heated to reflux and water removed using a Dean and Stark apparatus. Heating rate was adjusted to keep foaming down. Water evolution ceased after about 150 mL had been collected. A solid also formed in the stirred mixture. The mixture was heated at reflux for a further hour before slowly allowing to cool overnight. The solid was filtered off and pulled down hard for 30 minutes before washing with MTBE (2×1 L). The product was air dried at 40° C. (until constant weight was achieved) to give a near white solid (1330 g, 95% yield, single spot by TLC).

Benzyl-(benzotriazol-1-yl-[2-(pyridine-2-carbonyl)-phenylcarbamoyl]-methyl)-carbamate (9)

A mixture of crude compound 4 (2000 g, 10.09 mol) and compound 8 (3620 g, 11.09 mol) in DCM (36 L) was cooled to 0-5° C. in a 60 L reaction vessel. 4-Dimethylaminopyridine (148 g, 1.21 mol) was added in one lot. 1-(3-Dimethylaminopropyl)-3-ethylcarbodiimide hydrochloride (2417 g, 12.61 mol) was added in small portions over a 30-minute period while maintaining the temperature at 0-5° C. The mixture was stirred for a further hour at 0-5° C. to give a clear dark brown solution. TLC (elute 50% ethyl acetate in hexane) indicated that all compound 4 (Rf=0.7 yellow spot) had been consumed and compound 9 (Rf=0.35) had formed. Saturated sodium bicarbonate solution (20 L) was added and the mixture stirred for 5 minutes. The aqueous layer was removed and the organic layer dried over anhydrous sodium sulfate before evaporating under vacuum to give thick oil (about 7150 g, 140% crude yield).

Benzyl (2-oxo-5-pyridin-2-yl-2,3-dihydro-1H-benzo[e][1,4]diazepin-3-yl)-carbamate (10)

Crude compound 9 (about 7.15 kg) was dissolved in methanol (10 L) and stirred at room temperature. A solution of methanol saturated with ammonia (10 L) was added in one portion. The mixture was stirred for one hour at room temperature. TLC (elute 50% ethyl acetate in hexane) indicated that compound 9 (Rf=0.35) had eliminated benzotriazol (Rf=0.5) to give an un-cyclised intermediate (Rf=0.1). The mixture was initially warmed to about 30° C. and then allowed to stir overnight while cooling to room temperature. A solid formed in the stirred mixture. TLC (elute 50% ethyl acetate in hexane) indicated that the un-cyclised intermediate (Rf=0.1) had cyclised to form compound 10 (Rf=0.15). The slurry was filtered and the filter cake washed with cold methanol (1 L) followed by ethyl acetate (3 L) and finally hexane (2 L). The filtrate was stripped to about half its original volume and allowed to stand for two days. A second crop was filtered off (if formed) and washed with cold methanol, ethyl acetate and hexane. The combined good crops were air dried at 40-50° C. in a circulating air cabinet to give an off white solid (1785 g). The material can be slurried in two volumes of DCM, filtered and re-dried to improve purity if required. A total of 27.6 kg (92% HPLC purity) of crude compound 10 was made from 114.4 kg of crude compound 9 using the above method. A DCM slurry reduced the yield to 25.9 kg (98% HPLC purity; 42% yield over two steps from compound 4).

1H NMR (400 MHz, CDCl3) δ8.67 (1H,$), 8.61 (1H, d, J=4.1 Hz), 8.10 (1H, d, J=7.5 Hz), 7.84 (1H, dt J=1.4, 7.5 Hz), 7.50-7.28 (8H, m), 7.20 (1H, t, J=7.5 Hz), 6.99 (1H, d, J=7.5 Hz), 6.65 (1H, d, J=8.2 Hz), 5.37 (1H, d, J=8.2 Hz), 5.15 (2H, d, J=2.7 Hz)

Benzyl (1-[4-(tert-Butyl-dimethyl-silanyloxy)-3,3-dimethyl-2-oxo-butyl]-2-oxo-5-pyridin-2-yl-2,3-dihydro-1H-benzo[e][1,4]diazepin-3-yl)-carbamate (11)

Compound 10 (1040 g, 2.69 moles) was slurried in tetrahydrofuran (10.4 L) under a nitrogen atmosphere at 0-5° C. Potassium tert-Butoxide (423 g, 3.77 mol) was added in a single portion resulting in a 10° C. exotherm. A near clear solution formed briefly before another solid formed. The mixture was re-cooled to 0-5° C. Crude compound 3 (2080 g, 6.72 mol crude with 5.04 mol active content) was slowly added over a 30-minute period while maintaining the temperature at 0-5° C. Stirred for a further 30 minutes. The mixture was warmed to 20-25° C. and stirred for a further hour. TLC (elute 50% ethyl acetate in hexane) indicated that compound 12 (Rf=0.55) had formed but some compound 10 (Rf=0.15) remained. A silyl by-product spot (Rf=0.8) could also be seen. A further charge of potassium tert-butoxide (78 g, 0.70 mol) was added in one lot and the mixture stirred for 20 minutes. TLC check occasionally indicated that all of compound 10 had been consumed. If some compound 10 remains by TLC add extra crude compound 3 (200 g, 0.65 mol) stir for 10 minutes. Charge extra potassium tert-butoxide (78 g, 0.70 mol) and stir for 20 minutes. The reaction should now be complete but this step can be repeated until compound 10 is consumed. The mixture was stirred for a further hour and then allowed to stand overnight at room temperature. The reaction mixture was poured into 5% brine solution (20 L) and extracted with ethyl acetate (10 L and then 5 L). The combined organic extracts were washed with 5% brine solution (5 L) and then dried over anhydrous sodium sulfate. The solution was evaporated under vacuum to give viscous oil (sometimes containing some crystals). The oil was slowly poured into hexane (15 L) allowing time a solid to form. The resulting slurry was stirred for 2 hours to form a fine slurry. The mixture was filtered and washed with hexane (2×3 L). The filter cake was air dried at 20-30° C. in a circulating air cabinet to give a tan solid (1291 g, 78% yield, 97.6% HPLC purity).

$^1$H NMR (400 MHz, CDCl$_3$) δ8.63 (1H, d, J=4.8 Hz), 8.15 (1H, d, J=8.2 Hz), 7.81 (1H, t, J=7.5 Hz), 7.47 (1H, t, J=7.5 Hz), 7.42-7.28 (6H, m), 7.23 (1H, t, J=7.5 Hz), 7.10 (1H, d, J=8.2 Hz), 6.73 (1H, d, J=8.2 Hz), 5.49 (1H, d, J=8.2 Hz), 5.20-5.10 (3H, m), 4.45 (1H, d, J=17.7 Hz), 3.67 (2H, s), 1.24 (3H, s), 1.19 (3H, s), 0.90 (9H, s), 0.08 (3H, s), 0.05 (3H, s).

tert-Butyl (3-nitrophenyl)-carbamate (N2)

Triethylamine (915 g, 9.04 mol) and 4-(dimethylamino)-pyridine (30 g, 0.25 mol) was added to a solution of 3-nitroaniline (833 g, 6.03 mol) in tetrahydrofuran (6.1 L) at room temperature. The mixture was heated to reflux then external heating turned off. A solution of di-tert-butyldicarbonate (1448 g, 6.63 mol) in tetrahydrofuran (2.2 L) was added at such a rate to maintain reflux. The mixture was heated at reflux with external heating for a further 2 hours. TLC (elute 33% ethyl acetate in hexane) indicated that all the 3-nitroaniline (Rf=0.6) had been consumed and compound N2 (Rf=0.85) had formed. The mixture was allowed to cool to room temperature overnight. Solvent was evaporated under vacuum and the residue dissolved in DCM (15 L). The mixture was washed with water (2×8 L) then dried over anhydrous sodium sulfate. The DCM solution was passed through a silica gel plug (1 kg) and washed through with more DCM (5 L) to remove residual 4-(dimethylamino)-pyridine. The solution was evaporated under vacuum to give a thick slurry. Hexane (4 L) was added and the mixture allowed cool overnight. The mixture was filtered and washed with hexane (3 L). The filter cake was dried in a circulating air cabinet overnight to give a tan solid (1205 g, 84% yield, single spot by TLC).

tert-Butyl methyl-(3-nitrophenyl)-carbamate (N3)

A solution of tert-butyl-(3-nitrophenyl)-carbamate (904 g, 3.79 mol) in tetrahydrofuran (11.25 L) was cooled to 0-5° C. under a nitrogen atmosphere. Potassium tert-butoxide (555 g, 4.95 mol) was added in small portions over a one hour period while maintaining the temperature at <10° C. The mixture was then stirred at about 10° C. for 90 minutes before re-cooling back to 0-5° C. Dimethyl sulfate (622 g, 4.93 moles) was slowly added over a one hour period while maintaining the temperature at <10° C. The mixture was allowed to warm to room temperature while stirring overnight. TLC (elute 10% ethyl acetate in hexane) indicated that all N2 (Rf=0.35) had been consumed and N3 (Rf=0.45) had formed. The mixture was carefully poured into dilute ammonia solution (3 L of 33% w/w ammonia solution and 10 L of water) and stirred for one hour. The mixture was extracted into DCM (3×5 L). The combined organic extracts were washed with water (5 L) and then brine (5 L) before drying over anhydrous sodium sulfate. The mixture was evaporated under vacuum to give red/brown oil (943 g, 98% yield, 98.5% GC purity).

$^1$H NMR (400 MHz, CDCl$_3$) δ 8.14 (1H, t, J=2.1 Hz), 7.98 (1H, dd, J=8.1, 2.0 Hz), 7.61 (1H, d, J=8.1 Hz), 7.47 (1H, t, J=8.1 Hz), 3.31 (3H, s), 1.46 (9H, s).

tert-Butyl (3-aminophenyl)-methyl-carbamate (N4)

Triethylamine (30 mL) was added to a solution of tert-butyl methyl-(3-nitrophenyl)-carbamate (500 g, 1.98 mol) in methanol (2.5 L). Palladium on carbon (5% w/w; Johnson Matthey type 87L paste, 50% water; 50 g) was carefully added under a nitrogen atmosphere and the mixture hydrogenated using a Parr shaker at 50 psi hydrogen pressure. Hydrogen uptake was rapid and the mixture exothermed from 20° C. to 75° C. Hydrogenation was continued for one hour after the exotherm had ended. TLC (elute 89% chloroform, 10% methanol and 1% ammonia solution) indicated that N3 (Rf=0.75) had been consumed and N4 (Rf=0.55) had formed. The mixture was carefully filtered through a bed of celite on top of a GF-F fibre pad. The filtrate was evaporated under vacuum to dryness. The resulting solid residue was slurried in hexane (1000 mL) for one hour. The mixture was filtered and washed with hexane (500 mL). The product was dried in a vacuum oven at 40° C. to give a tan solid (429 g, 97% yield). 98.6% GC purity, melting range=100-102° C. (This hydrogenation has also been carried out at atmospheric pressure).

$^1$H NMR (400 MHz, CDCl$_3$) δ 7.09 (1H, t, J=7.9 Hz), 6.65-6.56 (2H, m), 6.5 (1H, dd, J=8.1, 2.0 Hz), 3.65 (2H, br s), 3.22 (3H, s), 1.45 (9H, s).

3-Amino-1-(4-acetoxy-3,3-dimethyl-2-oxo-butyl)-5-pyridin-2-yl-1,3-dihydrobenzo[e][1,4]diazepin-2-one (13-A)

A 45% w/v solution of hydrogen bromide in acetic acid (2080 mL, 11.6 mol) was diluted with more acetic acid (11 L) and stirred at room temperature. Compound 11 (2230 g, 3.63 mol) was added in one lot (with a 4° C. exotherm). The mixture was warmed to 35-40° C. for 2 hours. TLC (of a small sample neutralised with saturated sodium bicarbonate and extracted into dichloromethane, elute 5% methanol in dichloromethane) indicated that all of compound 11 (Rf=0.95) had been consumed and that only a small trace of Cbz protected intermediate (Rf=0.45) remained. The mixture was evaporated under vacuum (75° C./<100 mbar) to remove most of the acetic acid. The thick residue was dissolved in cold water (20 L) at <10° C. and washed with dichloromethane (2×8 L) to remove benzyl bromide and silyl by-products. Each dichloromethane wash was back extracted with water (3 L). Fresh dichloromethane (10 L) was added to the aqueous solution. Solid sodium bicarbonate was added to the stirred mixture until effervescence stopped and pH=8. The dichloromethane layer was removed and the aqueous layer extracted with more dichloromethane (5 L). The combined dichloromethane layers were dried over anhydrous sodium sulfate and evaporated under vacuum to give a thick oil. Ethyl acetate (5 L) was added to the oil while still in the rotating Rotavap flask. The oil dissolved and a solid crystallised out. The slurry was cooled to room temperature and filtered. The filter cake was washed well with cold ethyl acetate. The mother liquor was evaporated to produce a further crop. The product was dried at 35° C. in a circulating air cabinet to give an off white powder (1250 g, 84% yield, 98.6% HPLC purity).

$^1$H NMR (400 MHz, CDCl$_3$) δ 8.62 (1H, d, J=3.9 Hz), 8.17 (1H, d, 7.8 Hz), 7.81 (1H, dt, J=2.0, 7.8 Hz), 7.49 (1H, dt, J=2.0, 7.8 Hz), 7.42-7.33 (2H, m), 7.23 (1H, dt, J=1.0, 7.8 Hz), 7.09 (1H, d, J=8.3 Hz), 5.10 (1H, d, J=18.0 Hz), 4.67 (1H, s), 4.43 (1H, d, J=18.0 Hz), 4.18 (2H, q, J=10 Hz), 3.65 (2H, br s), 2.47 (1H, br s), 2.08 (3H, s), 1.32 (3H, s), 1.28 (3H, s).

(R)-3-Amino-1-(4-acetoxy-3,3-dimethyl-2-oxo-butyl)-5-pyridin-2-yl-1,3-dihydrobenzo[e][1,4]diazepin-2-one (R)-mandelic acid salt (14-A R-mandelate salt)

Small scale—Compound 13-A (28 g, 68.7 mmol) was slurried in acetonitrile (178 mL) at 20° C. R-mandelic acid (6.27 g, 41.1 mmol) was added and the mixture stirred until a clear solution formed. Diethyl ether (59 mL) was added before slowly cooling the mixture down to −5° C. The mixture was filtered and washed with ice cold 30% diethyl ether in acetonitrile (40 mL). The product was vacuum dried at 40° C. to give a near white solid (20.3 g, 43% ee R-isomer by chiral HPLC). The crude product was dissolved in acetonitrile (89 mL) at about 45° C. and allowed to slowly cool to 20° C. while standing over a 2 hour period. Fibre like crystals slowly formed. The mixture was filtered and washed with cold (−18° C.) acetonitrile (20 mL) followed by diethyl ether (40 mL). The product vacuum dried at 35° C. to give a white solid (8.2 g, 21% yield, 98.8% ee R-isomer by chiral HPLC).

Larger scale—Compound 13-A (1266 g, 3.10 mol) was slurried in acetonitrile (8050 mL) at 20° C. About half the solid seemed to dissolve. R-Mandelic acid (283 g, 1.86 mol, 0.6 molar equiv.) was added to the stirred mixture. The remaining solid slowly dissolved to form a clear yellow solution. Diethyl ether (2660 mL) was added. The solution remained clear at 20° C. The mixture was slowly cooled to −5° C. over a 30-minute period. As the temperature dropped below 5° C., the solution may be seeded with previously made R-mandelate salt. A very thick suspension forms (almost solidified) that slowly thinned out while stirring for a further 2 hours. The mixture was filtered (slow) and washed with cold (−18° C.) 50% acetonitrile in diethyl ether (1.5 L) and then with just diethyl ether (2.5 L). The product was dried at 35° C. in a circulating air cabinet overnight to give a near-white solid (1022 g slightly damp). The solid can be slightly gummy if any acetonitrile remains during air drying. Chiral HPLC indicated that the salt was composed of about 69% R-isomer and 32% S-isomer. The crude product (1022 g) was dissolved in acetonitrile (4.1 L) at about 45° C. Heated until just in solution and then allow to cool naturally immediately with only occasional mixing. Prolonged heating or overheating seemed to results in product decomposition. Once the temperature had dropped below 35° C. the solution may be seeded with previously made compound 14-A R-mandelate salt (>99% ee by chiral HPLC). The mixture was slowly cooled to about 20° C. over a 4-hour period with occasional stirring. The thick mixture was filtered and washed with cold (about −10° C.) acetonitrile (1 L) followed by diethyl ether (2 L). The product was dried at 35° C. in a circulating air cabinet overnight to give a white crystalline solid (461 g, 99.5% ee R-isomer by chiral HPLC, 26.5% yield).

Seeding with compound 14-A R-mandelate salt made by a procedure corresponding to that above can be used to expedite crystallisation, but is not essential.

(R)-3-Amino-1-(4-acetoxy-3,3-dimethyl-2-oxo-butyl)-5-pyridin-2-yl-1,3-dihydrobenzo[e][1,4]diazepin-2-one (14-A)

Compound 14-A R-mandelate salt (4474 g, 7.98 mol) was dissolved in a stirred mixture of saturated sodium bicarbonate (25 L) and dichloromethane (25 L) and stirred for 10 minutes. The aqueous layer was removed and back extracted with dichloromethane (5 L). The combined dichloromethane layers were washed with more saturated sodium bicarbonate solution (10 L). The new aqueous layer was back extracted with dichloromethane (5 L) again. The combined dichloromethane extracts were dried over anhydrous sodium sulfate. The free base solution was evaporated down to a volume of 15 L. This solution was assumed to contain 3260 g (7.98 mol) of compound 14-A. The solution was used directly in the next step. 99.6% HPLC purity, 99.3% ee R-isomer chiral HPLC purity.

$^1$H NMR (400 MHz, CDCl$_3$) δ 8.62 (1H, d, J=4.1 Hz), 8.17 (1H, d, J=7.5 Hz), 7.82 (1H, dt, J=1.3, 8.1 Hz), 7.50 (1H, dt, J=2.0, 7.8 Hz), 7.42-7.33 (2H, m), 7.23 (1H, t, J=6.8 Hz), 7.09 (1H, d, J=8.2 Hz), 5.10 (1H, d, J=18.0 Hz), 4.67 (1H, s), 4.43 (1H, d, J=18.0 Hz), 4.18 (2H, q, J=10 Hz), 2.48 (1H, br s), 2.08 (3H, s), 1.56 (2H, br s), 1.32 (3H, s), 1.28 (3H, s).

(R)-1-[1-(4-Acetoxy-3,3-dimethyl-2-oxo-butyl)-2-oxo-5-pyridin-2-yl-2,3-dihydro-1H-benzo[e][1,4]diazepin-3-yl]-3-(3-tert-butoxycarbonyl-methyl-amino-phenyl)-urea (18-A)

A slurry of 1,1'-carbonyldiimidazole (421 g, 2.60 mol) in DCM (3260 mL) was cooled to 0-5° C. while stirring under a nitrogen atmosphere. A solution of compound N4 (577 g, 2.60 mol) in DCM (1630 mL) was slowly added over a 30-minute period while maintaining the temperature at 0-5° C. The 1,1'-carbonyldiimidazole slowly dissolved to form a light orange solution during the addition. The solution was stirred at 0-5° C. for a further hour before warming to 15-20° C. and stirring for a further hour. A 21.73% w/v solution of compound 14A (3751 mL, containing 815 g, 2.00 mol) in DCM was slowly added over a 30-minute period while maintaining the temperature at 15-20° C. The mixture was stirred at this temperature for a further 2 hours. TLC (Small sample quenched into saturated sodium bicarbonate solution. Elute ethyl acetate) indicated that all of compound 14A (Rf=0.1) had been consumed and compound 18A (Rf=0.35) had formed. =The mixture was washed with saturated sodium bicarbonate solution (2×6 L). Each wash was back extracted with DCM (2 L). The combined DCM layers were dried over anhydrous sodium sulfate and evaporated under vacuum to give a thick oil (2020 g, still a little solvent-wet). Ethyl acetate (5 L) was added and evaporation continued to remove residual DCM from the mixture. The mixture was made-up to a volume of 7.25 L with ethyl acetate (a crude concentration of about 25% w/v). 85.8% HPLC purity with two earlier running components (6.9% and 0.8%) and two later running components (3.9% and 0.6%).

Purification of Compound 18-A

A chromatography column was wet packed with 3 kg of silica gel in 79% ethyl acetate, 20% hexane and 1% triethylamine (the triethylamine is used only during column packing). About 1000 mL of compound 18A solution (containing about 250 g of crude product) was diluted to 2000 mL with ethyl acetate and then hexane (500 mL) slowly added while stirring. This clear solution was charged onto the column. The column was eluted with 20% hexane in ethyl acetate (about 35 L required) until the less polar impurity was removed and then with ethyl acetate (about 35 L required) until compound 18A is removed. Good fractions were evaporated under vacuum to remove solvent. Evaporation was stopped while the product oil was still mobile and before a thick tar/glass formed. HPLC purity 96.8%.

$^1$H NMR (400 MHz, CDCl$_3$) δ 8.61 (1H, d, J=4.1 Hz), 8.15 (1H, d, J=7.5 Hz), 7.79 (1H, dt, J=2.0, 7.5 Hz), 7.51 (1H, t, J=7.9 Hz), 7.42-7.30 (3H, m), 7.26 (1H, t, J=7.5 Hz), 7.19 (1H, t, J=8.1 Hz), 7.13-7.05 (2H, m), 6.93 (1H, d, J=7.5 Hz), 6.86 (1H, br s), 6.75 (1H, d, J=8.1 Hz), 5.70 (1H, d, J=7.5 Hz), 5.03 (1H, d, J=18.4 Hz), 4.52 (1H, d, J=18.4 Hz), 4.16 (2H, q, J=11.0, 6.0 Hz), 3.21 (3H, s), 2.07 (3H, s), 1.45 (9H, s), 1.29 (3H, s), 1.26 (3H, s).

(R)-1-[1-(4-Acetoxy-3,3-dimethyl-2-oxo-butyl)-2-oxo-5-pyridin-2-yl-2,3-dihydro-1H-benzo[e][1,4]diazepin-3-yl]-3-(3-methylamino-phenyl)-urea (TR2-A)

Compound 18-A (1046 g) was dissolved in acetic acid saturated (about 1.5 molar) with hydrogen chloride (11 L) to give a light orange solution. The mixture exothermed from 15° C. to 23° C. The mixture was stirred at room temperature for 3 hours. TLC (small sample neutralised with sodium bicarbonate and extracted into DCM; elute: ethyl acetate) indicated that all of 18-A (Rf=0.35) had been converted into TR2-A (Rf=0.20). Nitrogen was bubbled through the solution for one hour to reduce hydrogen chloride content. Most of the acetic acid was removed under vacuum (65° C./<60 mmHg) to give a thick amber oil. The product was dissolved in DCM (10 L) and poured into a stirred saturated solution of sodium bicarbonate (15 L). More solid sodium bicarbonate was added until effervescence stopped and pH=8. (Do not use a stronger base than bicarbonate. Even carbonate will remove the acetate group). The DCM layer was removed and the aqueous layer re-extracted with DCM (2×2 L). The combined DCM extracts were dried over anhydrous sodium sulfate and filtered through a bed of celite. The DCM solution was evaporated under vacuum to give a foamed-up oil. Ethyl acetate (5.5 L) was added to the material while still in the rotating rotary evaporator flask with the vacuum off. The oil dissolved and a solid slowly formed. The mixture was allowed to cool to room temperature while standing overnight. The mixture was filtered and washed with ethyl acetate (4 L). The filter cake was pulled down hard and then dried in a vacuum oven at 35° C. overnight. The solid was broken-up and passed through a sieve before drying further in a vacuum at 35° C. for 2 days (no weight change between second and third day of drying) to give an off-white powder (740 g). TR2-A may be recrystallized from ethyl acetate, if required. A total of 3711 g (84% yield, 98.2% HPLC purity, 99.9% ee R-isomer chiral HPLC purity) of compound TR2-A was made from about 5234 g of compound 18-A using the above method.

$^1$H NMR (500 MHz, CDCl$_3$) δ 8.60 (1H, d, J=4.9 Hz), 8.15 (1H, d, J=7.9 Hz), 7.77 (1H, dt, J=1.8, 7.9 Hz), 7.49 (1H, dt, J=1.8, 7.9 Hz), 7.38 (1H, dd, J=1.8, 7.9 Hz), 7.33 (1H, ddd, J=1.2, 4.9, 7.3 Hz), 7.25 (with CHCl$_3$ peak, t, J=7.3 Hz), 7.10 (1H, d, J=7.3 Hz), 7.03-6.93 (3H, m), 6.75 (1H, t, J=2.1 Hz), 6.52 (1H, dd, J=1.8, 7.3 Hz), 6.28 (1H, dd, J=1.8, 7.9 Hz), 5.72 (1H, d, J=7.9 Hz), 4.96 (1H, d, J=18.0 Hz), 4.50 (1H, d, J=18.0 Hz), 4.14 (2H, q, J=10.6 Hz), 3.73 (1H, br s), 2.77 (3H, s), 2.05 (3H, s), 1.26 (3H, s), 1.23 (3H, s).

(R)-1-[1-(4-Hydroxy-3,3-dimethyl-2-oxo-butyl)-2-oxo-5-pyridin-2-yl-2,3-dihydro-1H-benzo[e][1,4]diazepin-3-yl]-3-(3-methylamino-phenyl)-urea (TR2)

Compound 18-A was dissolved in acetic acid saturated with hydrogen chloride at about 20° C. and stirred for about 3 hours. Most of the acetic acid was removed from the mixture under reduced pressure before dissolving the residue in water. The mixture was neutralised with sodium bicarbonate and then extracted into dichloromethane. The combined extracts were dried over anhydrous sodium sulphate and then evaporated under reduced pressure to give a glass-like oil TR2-A, which was used directly in the next step.

TR2-A was dissolved in methanol. A solution of potassium carbonate in water was added and the mixture stirred at about 20° C. for about 2 hours. Most of the methanol was removed from the mixture under reduced pressure before dissolving the residue in water. The mixture was extracted into dichloromethane. The combined extracts were dried over anhydrous sodium sulphate and then evaporated under reduced pressure to give a yellow glass-like oil. The yellow oil was purified by flash column chromatography through silica gel, using gradient elution (1-3% methanol in dichloromethane). Good fractions were evaporated under vacuum to give TR2 as a pale yellow glass-like solid.

$^1$H NMR (400 MHz, CD$_3$Cl$_3$) δ 8.60 (1H, d, J=4.0 Hz); 8.12 (1H, d, J=11.2 Hz); 7.78 (1H, dt, J=8.0 and 2.4 Hz); 7.52 (1H, dt, J=7.2 and 2.0 Hz); 7.39-7.32 (2H, m); 7.28-7.23 (1H, m); 7.20 (1H, d, J=10.0 Hz); 7.04 (1H, t, J=8.0 Hz); 6.94-6.85 (2H, m) 6.76 (1H, t, J=2.0 Hz); 6.55, 6.30 (2H, 2×dd, J=8.0, 2.0 Hz and 8.4, 3.2 Hz); 5.70 (1H, d, J=7.8 Hz); 4.91, 4.49 (2H, AB system, J$_{AB}$=22.0 Hz); (2H, AB system, J$_{AB}$=14.0 Hz); 3.16 (1H, br s); 2.78 (3H, s); 1.20, 1.19 (6H, 2×s).

Exact mass by positive ion electrospray mass spectroscopy M+H=515.2398 m/z (theory: 515.2407 m/z for composition C$_{28}$H$_{31}$N$_6$O$_4$).

Example 2: Synthesis of (TR2-A) Via tert-butyl(3-hydroxycarbamoylphenyl)methylcarbamate (N1)

Compound (TR2-A) was synthesized according to Scheme 5 below.

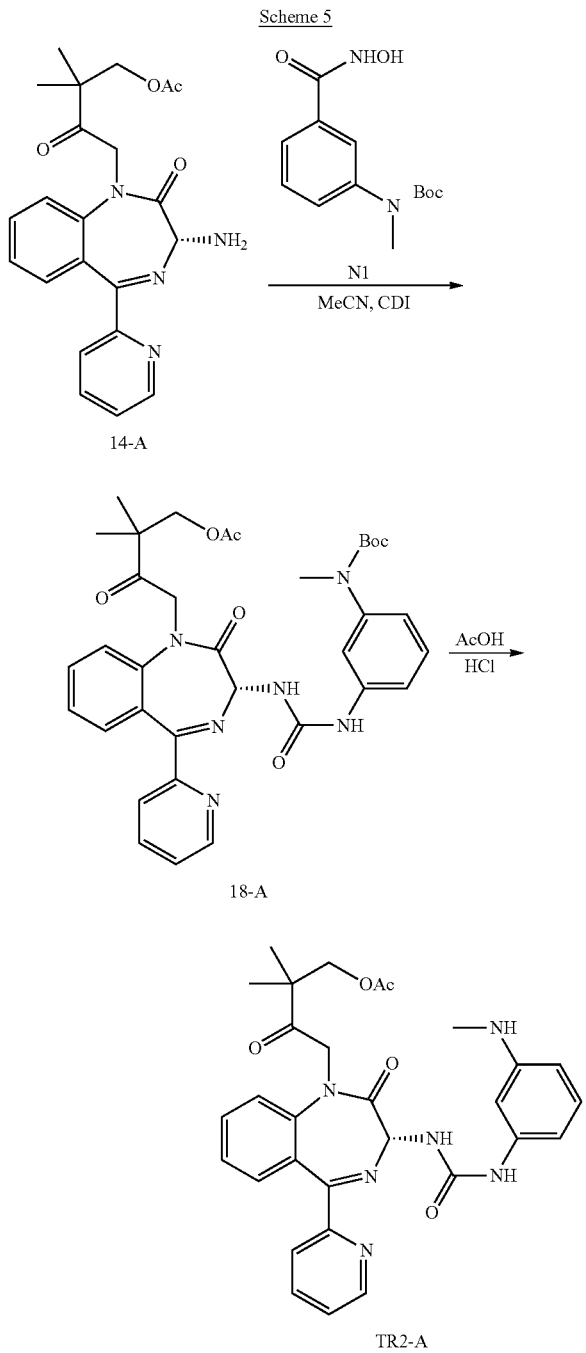

Compound N1 was synthesized according to Scheme 6 below.

Scheme 6

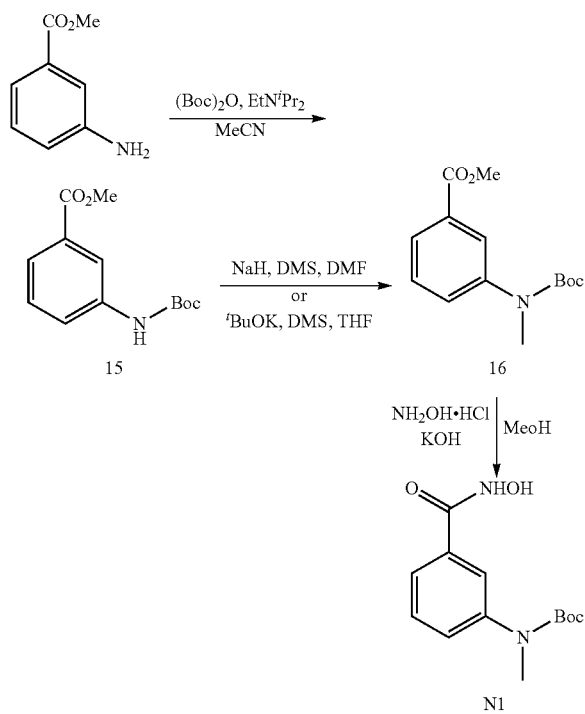

Scheme 6 illustrates synthesis of N1 via 15 and 16. Whilst exemplary reagents are illustrated in Scheme 6, it will be appreciated that these may be varied. For example, Boc in 15 to N1 may be replaced with an alternative amino protecting group, such as Fmoc, Cbz or Ac. Conversion of methyl 3-aminobenzoate to 15 could, for example, use organic bases other than DIPEA, e.g. triethlyamine. The methylation of 15 to 16, preferably involves use of a base (e.g. KO$^t$Bu or NaH) and a methylating agent (e.g. DMS or MeI). The solvent in this step may be an aprotic solvent, preferably a polar aprotic solvent (e.g. DMF or THF). Conversion of 16 to N1 may be performed with a hydroxylamine salt (e.g. an HCl or sulphate salt) or hydroxylamine solution, a base (e.g. KOH) and a protic solvent (e.g. methanol).

Methyl 3-(tert-butoxycarbonylamino)benzoate (15)

To a 20.0 L, 3-necked round bottomed flask equipped with overhead stirrer, thermometer, nitrogen bubbler and reflux condenser was charged acetonitrile (6.5 L), methyl-3-aminobenzoate (848 g, 5.6 mol), N,N-diisopropylethylamine (1.44 kg, 11.2 mol, 2.0 equivalents) and di-tert-butyldicarbonate (2.0 kg, 9.16 mol, 1.63 equivalents). A nitrogen atmosphere was established and stirring was commenced. The vessel contents were heated at 70° C. for 3 days after this time TLC (eluent: 1:1 hexane/ethyl acetate) revealed no starting material remaining. Heating was then discontinued and the vessel contents cooled to −50° C. and transferred to a 20 L rotary evaporator. Solvent was removed under reduced pressure and the resulting beige/orange residue was triturated with hexane (4.0 L) for 1 hour prior to filtration of the resulting solid. The recovered solid was re-slurried in hexane (4.0 L) overnight, filtered, washed on the funnel with hexane (2×0.5 L) and pulled dry. Damp weight yield=1213 g. The solid was dried in a vacuum oven at 40° C. (48 hours) to constant weight. Dried weight yield=1185 g, 84.2%. This material was used directly in the next stage.

$^1$H NMR (400 MHz, CDCl$_3$) δ 12.10 (1H, br s), 7.99 (1H, s), 7.91 (1H, d, J=7.5 Hz), 7.55-7.50 (1H, m), 7.43 (1H, t, J=7.5 Hz), 3.31 (3H, s), 1.47 (9H, s) ppm.

Methyl 3-(tert-butoxycarbonylmethylamino)benzoate (16)

To a 20 L, flange flask equipped with overhead stirrer, thermometer and 500 mL P-E dropping funnel was dissolved a solution of compound 15 (1075 g, 4.28 mol) in DMF (13.4 L). Stirring was commenced and the vessel contents were cooled to 0-10° C. in an ice/water/salt bath. Sodium hydride (60% dispersion in oil) (256 g, 6.42 mol, 1.5 equivalents) was added portion wise over 20 minutes maintaining the internal temperature at <10° C. Once complete, the reaction mixture was warmed to ambient, stirred for 1 hour and then re-cooled to 0-10° C. Dimethyl sulphate (863 g, 6.84 mol, 1.6 equivalents) was added over 30 minutes and then the cooling bath was removed and flask contents warmed to ambient. After this time TLC (eluent: 9:1 hexane/ethyl acetate+ninhydrin) revealed the desired product (3) with no starting material remaining. The reaction mixture was then cautiously quenched into 6 M aqueous ammonia solution (18.0 L [12.0 L water+6.0 L of 0.880 ammonia]) and stirring of the resulting mixture was continued for 1 hour. After this time DCM (10.0 L) was added and stirring continued for an additional 30 minutes. The bi-phasic layers were separated and the upper aqueous layer was back extracted with DCM (5.0 L). The combined organic layers were back washed with water (5.0 L) and 5% w/w brine solution (5.0 L). The organic layer was concentrated on the rotary evaporator to ~2.5 kg and then washed with water (2×10.0 L). The concentrate was then re-stripped under high vacuum (~50 mbar) to give a brown red oil. Total yield of compound 16=1270 g, 112%. Residual mineral oil from the sodium hydride was found to be present in the product (as seen by $^1$H NMR) but as this posed no risk to ongoing processing then no further purification of this material was undertaken and it was used directly in the next stage. NMR conformed to the required structure.

$^1$H NMR (400 MHz, CDCl$_3$) δ7.90 (1H, s), 7.82 (1H, d, J=8.0 Hz), 7.48-7.35 (2H, m), 3.90 (3H, s), 3.27 (3H, s), 1.44 (9H, s) ppm.

tert-Butyl-(3-hydroxycarbamoylphenyl)methylcarbamate (N1)

To a 20 L, flange flask equipped with overhead stirrer, thermometer and reflux condenser was charged methanol (3.7 L) and hydroxylamine hydrochloride (644 g, 9.27 mol, 2.0 equivalents). Stirring was commenced and the vessel contents heated to near reflux to dissolve the solid. The reaction mixture was then cooled to ~40° C. and a pre-prepared solution of potassium hydroxide (779 g, 13.89 mol, 3.0 equivalents) dissolved in methanol (2.5 L) was added in one portion. The vessel contents were then cooled to room temperature and compound 16 (1229 g, 4.63 mol, 1.0 equivalents) was added in one portion and stirring continued for 2 hours. After this time TLC (eluent: 9:1 DCM/methanol) revealed residual starting material remaining and hence the reaction mixture was warmed to 35-40° C. for an additional 2 hours. TLC revealed no starting material remaining and after cooling to room temperature the reaction mixture was neutralised by the addition of acetic acid (612 g, 10.19 mol, 2.2 equivalents). The mixture was then poured into water (20.0 L) and extracted with ethyl acetate (3×8.0 L). The combined organic layers were back washed with 25% w/w brine solution (2×5.0 L) and dried over sodium sulphate, filtered and filtrate stripped on the rotary evaporator (50° C.) to a thick paste. Hexane (2.5 L) was added to the warm paste before cooling to room temperature. The resulting slurry was filtered, washed on the funnel with hexane (2×0.5 L) and pulled dry. The colourless solid was air dried in a vacuum oven [no heat] until constant weight. Total yield=847 g, 69%. NMR conformed to the required structure.

$^1$H NMR (400 MHz, CDCl$_3$) δ 8.98 (1H, br s), 7.66 (1H, s), 7.48 (1H, d, J=7.5 Hz), 7.42-7.30 (2H, m), 3.25 (3H, s), 1.47 (9H,$) ppm.

(R)-1-[1-(4-Acetoxy-3,3-dimethyl-2-oxo-butyl)-2-oxo-5-pyridin-2-yl-2,3-dihydro-1H-benzo[e][1,4]diazepin-3-yl]-3-(3-tert-butoxycarbonyl-methyl-amino-phenyl)-urea (18-A)

Compound N1 (8.50 g, 31.92 mmol, 1.3 molar equiv.) was slurried in acetonitrile at room temperature. Carbonyldiimidazole (5.20 g, 32.07 mmol, 1.3 molar equiv.) was added in one lot (no exotherm noted) resulting in a clear solution. The solution was stirred at room temperature for 30 minutes and then heated to 60° C. for one hour before re-cooling to room temperature. TLC indicated that all N1 had been consumed. Compound 14-A (10.0 g, 24.48 mmol) was added and the mixture stirred at room temperature for 2 hours. TLC indicated all but a small trace of 14-A had been consumed and a new relatively clean product had formed. Most of the acetonitrile was removed under vacuum at 35° C. to give a thick oil (no change seen by TLC). The residual oil was dissolved in dichloromethane (200 mL) and washed with saturated sodium bicarbonate solution (2×150 mL). Dried over anhydrous sodium sulphate and stripped to a pinkish foamed-up oil (27.3 g). HPLC indicated this to be 45.4% compound 18-A with a 31.3% major impurity.

Preparation of TR2-A from Crude Compound 18-A (Made Via the Lossen Method)

Crude compound 18-A (25 g) was dissolved in acetic acid saturated with hydrogen chloride (250 mL) and stirred at room temperature overnight. TLC indicated that the reaction was complete by comparison with previously prepared reference samples. Most of the acetic acid was removed under vacuum at 50° C. to give a viscous oil. The oil was dissolved in water (250 mL) and neutralised by addition of solid sodium bicarbonate while stirring. The mixture was extracted with dichloromethane (2×250 mL) and the combined extracts dried over anhydrous sodium sulphate before evaporating solvent under vacuum to give a foam/glass (18.1 g). TLC indicated clean conversion. HPLC indicated the product to be 40.9% TR2-A and 32.3% impurity. Following flash chromatography HPLC indicated 69.0% TR2-A and 20.9% impurity.

Example 3: Alternative Synthesis of 2-(2-aminobenzoyl)pyridine (4)

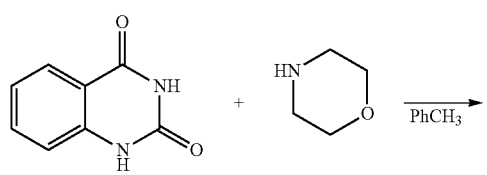

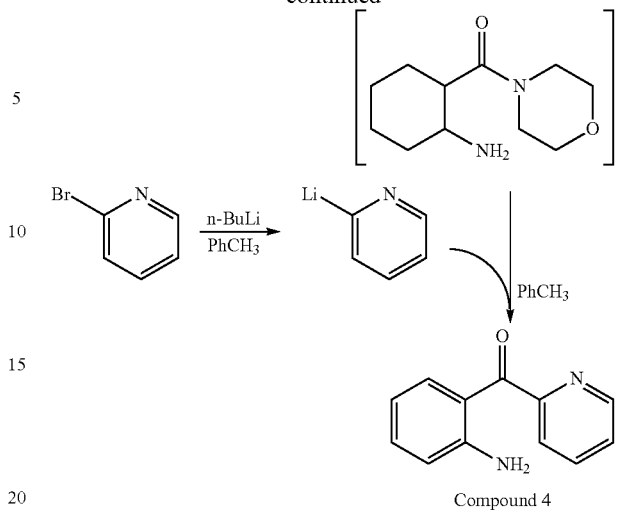

Compound 4

A solution of morpholine (855 g, 9.81 mol) in toluene (10 L) was stirred to 90° C. while adding isatoic anhydride (1600 g, 9.81 mol) in 25 g portions over a 2.5 hour period.

Carbon dioxide was rapidly evolved during the addition. The resulting mixture (referred to below as the morpholide solution) was stirred at 90° C. for a further hour before cooling to room temperature.

In a separate vessel a solution of 2-bromopyridine (3580 g, 22.66 mol) in toluene (12 L) was cooled to <−60° C. under a nitrogen atmosphere. n-Butyl lithium (1.6 M in hexane) (14.10 L, 22.56 mol) was slowly added over a 2-hour period while maintaining the temperature at <−60° C. The mixture was stirred at <−60° C. for a further 30 minutes. The previously prepared morpholide solution was slowly added over a 4-hour period while maintaining the temperature at <−60° C. The mixture was allowed to warm slowly to room temperature while stirring overnight.

The reaction mixture was added to a stirred mixture of hydrochloric acid (32%) (6.5 L), ice (6 kg) and water (6 L). The aqueous layer was removed and filtered. More ice (8 kg) was added followed by the slow addition of ammonium hydroxide (33%) (about 3.0 L) until pH=9. The resulting solid was filtered and washed with water. The filter cake was dried to give 2-(2-aminobenzoyl)pyridine (compound 4) as a yellow/brown solid (1630 g) in 80% crude yield.

Example 4: Solubility Study

A solubility study confirmed that (TR1) and (TR2-A) are more soluble in aqueous solution than YF476; and (TR2-A) is more soluble in aqueous solution than (TR1).

The test compound (2.5 mg of solid; n=1) was weighed in a clear glass vial and Britton-Robinson's buffer (0.5 mL) was added (pH 2.01, pH 3.06, pH 4.06, pH 5.08, pH 5.99, pH 6.98, and pH 8.16). The solution was agitated at ambient temperature overnight using a vial roller system, and then filtered (0.45 μm pore size; without pre-saturation). Two aliquots (50 μL) were sampled from the filtrate and diluted with one volume of 0.1 N hydrochloric acid and methanol (1:1 v/v) before analysis by HPLC-UV. A standard was prepared in DMSO at 10 mg/mL (n=1) which was then diluted 10-fold in 0.1 N hydrochloric acid and methanol (1:1 v/v) to give a 1 mg/mL solution. The concentration of test compound in the filtrate was quantified relative to the concentration standard.

Analysis was done using a gradient HPLC-UV system with a total cycle time of 6 min. The UV detection between 220 nm and 300 nm was done using a photodiode array detector. Total response was monitored.

| | Aqueous solubility | | | Solubility advantage | | |
|---|---|---|---|---|---|---|
| pH | YF476 (μg/mL) | (TR1) (μg/mL) | (TR2-A) (μg/mL) | ((TR1)/ YF476) | ((TR2-A)/ YF476) | ((TR2-A)/ TR1) |
| 2.01 | 2650 | 5000 | 4190 | 1.9 | 1.6 | 0.8 |
| 3.06 | 99.7 | 645 | 730 | 6.5 | 7.3 | 1.1 |
| 4.06 | 5.9 | 58.2 | 218 | 9.9 | 36.9 | 3.7 |
| 5.08 | 1.4 | 9.8 | 56 | 7 | 40.0 | 5.7 |
| 5.99 | 1.3 | 11.6 | 47.2 | 8.9 | 36.3 | 4.1 |
| 6.98 | 1.4 | 5.84 | 51 | 4.2 | 36.4 | 8.7 |
| 8.16 | 1.5 | 7.81 | 45.4 | 5.2 | 30.3 | 5.8 |

The solubility advantage of (TR1) and (TR2-A) over YF476 is especially pronounced at pH 4-6, which is the pH range of the part of the small intestine—duodenum to terminal jejunum or mid ilium—where most drug absorption takes place. This enhanced solubility is an indicator that (TR1), (TR2), (TR3) and (TR2-A) are likely to be more bioavailable, and therefore better drug candidates than YF476.

The values given in the table above are for crystalline YF476 and (TR2-A) and amorphous (TR1).

Crystalline (TR2-A) had almost the same solubility profile as amorphous (TR1), and is therefore likely to have comparable oral bioavailability. This is surprising because crystalline YF476 is poorly bioavailable and had to be converted to an amorphous form (spray-dried dispersion) to increase solubility and oral bioavailability. This should not be necessary with (TR2-A).

| | Aqueous solubility | |
|---|---|---|
| pH | (TR2-A) amorphous (μg/mL) | (TR2-A) crystalline (μg/mL) |
| 2.01 | 5000 | 4190 |
| 3.06 | 683 | 730 |
| 4.06 | 282 | 218 |
| 5.08 | 128 | 56 |
| 5.99 | 53.4 | 47.2 |
| 6.98 | 43 | 51 |
| 8.16 | 40.2 | 45.4 |

Example 5: Morphology Studies

In contrast to YF476, studies indicate that (TR1) and the pure enantiomers (TR2) and (TR3) prefer an amorphous state over a crystalline state.

Initial attempts to crystallise (TR2) and (TR3) were unsuccessful, indicating preference for an amorphous state. Indeed, XRPD analysis of (TR2) confirmed an amorphous state. This is indicative of an advantage over YF476 in terms of the formulation of a suitable pharmaceutical composition. YF476 is crystalline, which contributes to poor solubility and bioavailability. Amorphous YF476 can be used to increase bioavailability, but requires stabilization, which can be achieved as a solid dispersion on hydroxypropyl methyl cellulose by spray-drying. Formulation of (TR) (in racemic, non-racemic or enantiomerically pure form), which prefers an amorphous state, would avoid the need for this stabilization.

Example 6: CCK Receptor Antagonism (TR2) and (TR3) were compared with YF476 and YM022 in $CCK_1$ and $CCK_2$ receptor functional assays with the following assay criteria.

| Receptor assay (antagonist effect) | Source | Stimulus | Incubation | Measured component | Detection method |
|---|---|---|---|---|---|
| $CCK_1$ (human) | Human recombinant (CHO cells) | CCK-8s (300 nM) | 10 min 37° C. | cAMP | HTRF |
| $CCK_2$ (human) | Human recombinant (CHO cells) | CCK-8s (10 nM) | 10 min 37° C. | cAMP | HTRF |

HTRF: Homogeneous time-resolved fluorescence
cAMP: cyclic adenosine monophosphate
CHO: Chinese hamster ovary The results of the assays are shown in the table below:

| | $CCK_1$ | | $CCK_2$ | | Selectivity | |
|---|---|---|---|---|---|---|
| Antagonist | $IC_{50}$ (nM) | $K_B$ (μM) | $IC_{50}$ (nM) | $K_B$ (nM) | $IC_{50}(CCK_1)/$ $IC_{50}(CCK_2)$ | $K_B$ $(CCK_1)/$ $(CCK_2)$ |
| YF476 | 160 | 24 | 0.52 | 0.064 | 308 | 375 |
| TR2 | 1000 | 150 | 2.5 | 0.31 | 400 | 484 |
| TR3 | 8500 | 1300 | 99.0 | 12.0 | 86 | 108 |
| YM022 | — | — | 0.55 | 0.68 | — | — |

(TR2) and (TR3) were potent $CCK_2$ receptor antagonists and less potent $CCK_1$ receptor antagonists. In the $CCK_2$ assay, (TR2) compared favourably to YF476 and YM022: (TR2) was only about 5-fold less potent than YF476 and YM022; and although affinity of (TR2) for the $CCK_2$ receptor was about 5-fold lower than that of YF476, it was twice that of YM022. Furthermore, the selectivity of (TR2) for the $CCK_2$ receptor over the $CCK_1$ receptor was 30% higher than the selectivity of YF476. The potency of the antagonists is expressed as $IC_{50}$, the concentration of antagonist that causes a half-maximum inhibition of the control agonist response. The affinity of the antagonist for the receptor is expressed as $K_B$, the concentration of antagonist, which would occupy 50% of the receptors at equilibrium.

Example 7: Receptor Binding Screen

The potential of (TR2) and (TR3) to bind to other cellular and nuclear receptors was tested in a panel of 80 receptors. The assay used radiolabelled receptor ligands (agonist or antagonist, depending on the receptor), and the ability of the test compounds to inhibit ligand binding was measured by scintillation counting. No significant receptor binding (other than $CCK_2$ and $CCK_1$) was found.

Example 8: Pre-Clinical Studies: Proliferation of Cells In Vitro

The potency of (TR2) and (TR3) was tested in a sulphorhodamine-B (SRB) proliferation assay in a human gastric adenocarcinoma cell line stably transfected with the human gastrin/$CCK_2$ receptor gene ($AGS_{GR}$). SRB is a fluorescent dye that binds to proteins, so cells with a high rate of protein synthesis (proliferative cells) will show high levels of fluorescence in the SRB assay. The gastrin fragment G17 has an anti-proliferative effect on $AGS_{GR}$ cells. So, when treated with G17, the cells show lower levels of fluorescence in the SRB assay. (TR2) and (TR3) were compared with the positive controls YF476 and YM022. (TR2), YF476 and YM022, at a concentration of 100 nM, all completely inhibited the anti-proliferative effects of G17 (10 nM). (TR3), at a concentration of 500 nM, had the same effect. None of the compounds tested affected $AGS_{GR}$ cell proliferation in the absence of G17.

Example 9: Pre-Clinical Studies: Rats with a Gastric Fistula

The effect of subcutaneous injections of YF476, (TR2) and (TR3) on pentagastrin-stimulated gastric acid secretion was tested in conscious rats with a chronic gastric fistula. All treatments dose-dependently inhibited the acid secretion response. $ED_{50}$ values for YF476, (TR2), and (TR3) were 0.012, 0.03 and 0.3 μmol/kg, respectively.

Example 10: Pharmacokinetics in Healthy Subjects

In an initial study, healthy volunteers took a single oral dose of 100 mg (TR2) as an active pharmaceutical ingredient (API) in a capsule. Plasma concentrations were measured. The area under the curve of plasma concentrations of (TR2) after a single oral dose of 100 mg of active pharmaceutical ingredient (AUC=439.1) was about twice that observed for a similar formulation of a single oral dose of YF476 100 mg (AUC=198.5). Thus, (TR2) was observed to be more bioavailable than YF476.

In further clinical studies, healthy volunteers (n=8) took single oral doses of 5, 15, 50 and 100 mg (TR2) as an active pharmaceutical ingredient (API) in a capsule. Plasma concentrations were measured. The mean area under the curve (AUC) of plasma concentrations of (TR2) after a single oral dose of 100 mg of API ($AUC_{0-24\ h}$ (ng h/mL)=241.5) was about three times that observed for a similar formulation of a single oral dose of YF476 100 mg ($AUC_{0-24\ h}$=81.3; n=10). Thus, (TR2) was observed to have better oral bioavailability than YF476 in the healthy subjects.

Healthy volunteers (n=8) took single oral doses of 5, 15, 25 and 50 mg (TR2) as API in a capsule (TR2-A (crystalline) in hard gelatin capsules with no excipient, no processing of the API). Plasma concentrations of (TR2) and (TR2-A) were measured. The area under the curve of plasma concentrations of (TR2) after a single oral dose of 50 mg of (TR2-A) API ($AUC_{0-24\ h}$=212.5) was about the same as that observed for a similar formulation of a single oral dose of (TR2) 100 mg ($AUC_{0-24\ h}$=241.5). Thus, (TR2-A) was observed to have better oral bioavailability than (TR2) in the healthy subjects. Moreover, the plasma concentrations of (TR2-A) were low ($AUC_{0-24\ h}$<10), showing that (TR2-A) is acting as a prodrug for (TR2).

Example 11: Clinical Studies: Pharmacodynamic Effect in the Healthy Subject

Pentagastrin induces gastric acid secretion, and thereby increases $H^+$ concentration. In an initial study, in a healthy volunteer, single oral doses of 5, 25 and 100 mg of (TR2) administered in conjunction with pentagastrin infusion were observed to cause similar dose-dependent inhibition of the increase in $H^+$ concentration of gastric aspirate induced by the intravenous infusion of pentagastrin as observed for corresponding dosing of YF476 with pentagastrin infusion. Thus, the potency of (TR2) as a $CCK_2$ receptor antagonist was similar to that of YF476 in the healthy subject.

In further clinical studies, in healthy volunteers, single oral doses of 5, 15, 50 and 100 mg of (TR2) or 5, 15, 25 and 50 mg (TR2-A) were administered in conjunction with pentagastrin infusion (i.v. dose 0.6 μg/kg/h for 2 h). (TR2) and (TR2-A) were observed to cause similar dose-dependent inhibition of the increase in $H^+$ concentration of gastric aspirate induced by the intravenous infusion of pentagastrin as observed for dosing of YF476 with pentagastrin infusion. 100 mg of (TR2) and 50 mg (TR2-A) caused similar inhibition of the increase in $H^+$ concentration of gastric aspirate induced by the intravenous infusion of pentagastrin as observed for dosing of 100 mg YF476. Thus, the potency of (TR2) as a $CCK_2$ receptor antagonist was similar to that of YF476 in healthy subjects, and the potency of (TR2-A) is greater than that of both (TR2) and YF476. The observed results showed that (TR2) suppresses the effect of pentagastrin in a dose-dependent manner, and that a lower dose of (TR2-A) than (TR2) was required for full suppression.

Embodiments of the invention have been described by way of example and these embodiments are to be considered as illustrative rather than restrictive. It will be appreciated that variations in form and detail can be made without departing from the true scope of the invention, which is to be defined by the appended claims.

The invention claimed is:
1. A process for producing a compound of formula (I):

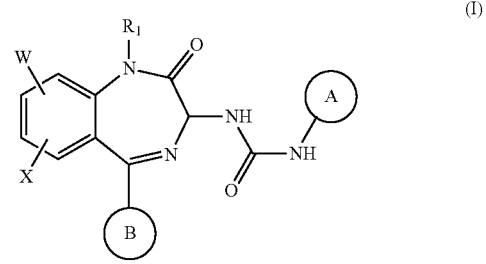

or a pharmaceutically acceptable salt thereof, wherein
$R_1$ is —$CH_2C(O)C(R_2)(R_3)$-L-$R_4$, —$CH_2CHOHC(R_2)$ $(R_3)$-L-$R_4$, —$CH_2CHOH(CH_2)_aR_7$, —$CH_2C(O)$ $(CH_2)_aR_8$, or an optionally substituted aliphatic moiety;
$R_2$ and $R_3$ are each, independently, H, $C_{1-3}$ aliphatic, halo, or $C_{1-3}$ haloaliphatic;
or $R_2$ and $R_3$ together with the intervening carbon atom to which they are bonded, form a $C_{3-6}$ carbocyclic moiety;
L is a bond or $C_{1-3}$ alkylene;
$R_4$ is —$OR_5$ or —$SR_5$;
$R_5$ is hydrogen, optionally substituted alkyl, a protecting group or —$C(O)R_6$;
$R_6$ is optionally substituted aliphatic, heteroaliphatic, aromatic or heteroaromatic moiety;
a is 0 or 1;
$R_7$ and $R_8$ are selected from alkyl, cycloalkyl groups, and saturated heterocyclic groups optionally substituted at a heteroatom;
W and X are, independently, hydrogen, halo, $C_{1-8}$ alkyl or $C_{1-8}$ alkoxy; and
rings A and B are each, independently, a monocyclic aryl or heteroaryl, optionally substituted with one or more substituents independently selected from halo, hydroxy, amino, nitro, carboxyl, carboxamido, cyano, —SO$_3$H, optionally substituted C$_{1-8}$ alkyl, C$_{1-8}$ alkoxy, C$_{1-8}$ alkylamino or di(C$_{1-8}$ alkyl)amino; wherein any one or more substituent on R$_1$, ring A or ring B may be unprotected or in a protected form;

wherein the process comprises:

providing a reaction mixture by adding a compound of formula (I-C):

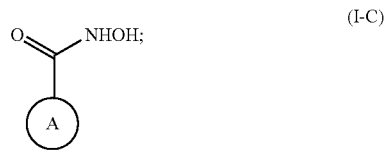

and a phosgene synthetic equivalent or phosgene, to an aprotic solvent and, subsequently, adding a compound of formula (I-B):

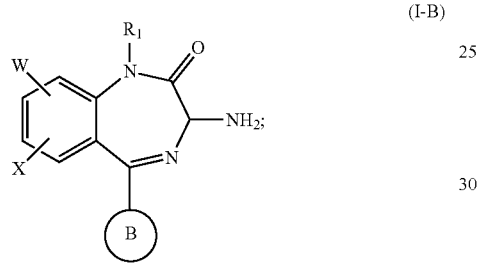

to the reaction mixture to form a compound of formula (I); wherein the phosgene synthetic equivalent is carbonyldiimidazole (CDI), diphosgene, triphosgene, a chloroformate, or disuccinimidyl carbonate.

2. The process of claim 1, wherein the process comprises providing a reaction mixture by adding a compound of formula (I-C) and a phosgene synthetic equivalent or phosgene, to an aprotic solvent and, subsequently, adding a compound of formula (I-B) to the reaction mixture to form a compound of formula (I), wherein the phosgene synthetic equivalent is carbonyldiimidazole, diphosgene, triphosgene, a chloroformate or disuccinimidyl carbonate.

3. The process of claim 1, wherein the phosgene synthetic equivalent or phosgene is carbonyldiimidazole.

4. The process of claim 1, wherein the process comprises the additional step of deprotection to remove one or more protecting groups, wherein any one or more substituents on R$_1$, ring A or ring B is in a protected form.

5. The process of claim 1, wherein the aprotic solvent is dichloromethane, acetonitrile, or toluene.

6. The process of claim 1, wherein R$_1$ is —CH$_2$C(O)C(R$_2$)(R$_3$)-L-R$_4$.

7. The process of claim 1, wherein:
(a) at least one of ring A and ring B is unsubstituted or substituted phenyl or pyridyl; and/or
(b) W and X are, independently H, halo, C$_{1-3}$ alkyl or C$_{1-3}$ alkoxy.

8. The process of claim 1, wherein:
(a) at least one of ring A and ring B is unsubstituted, monosubstituted or disubstituted phenyl or unsubstituted, monosubstituted or disubstituted 2-, 3- or 4-pyridyl: and/or
(b) W and X are both H.

9. The process of claim 1, wherein ring A is phenyl having a meta substituent chosen from NHMe, NMeEt, NEt$_2$, F, Cl, Br, OH, OCH$_3$, NH$_2$, NMe$_2$, NO$_2$, Me, (CH$_2$)$_n$—CO$_2$H, CN, CH$_2$NMe$_2$, NHCHO and (CH$_2$)$_n$—SO$_3$H where n is 0-2; unsubstituted phenyl, or 2-, 3- or 4-pyridyl optionally substituted with a substituent selected from F, Cl, CH$_3$ and CO$_2$H; ring B is 2-, 3- or 4-pyridyl or phenyl.

10. The process of claim 1, wherein the compound of formula (I) is a compound of formula (II):

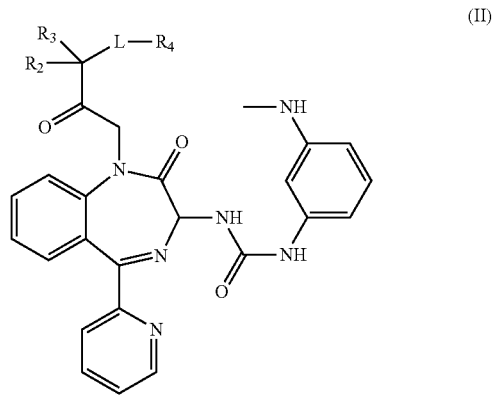

or a pharmaceutically acceptable salt thereof, wherein R$_2$, R$_3$, L and R$_4$ are as defined in claim 1, the compound of formula (I-B) is a compound of formula (II-B):

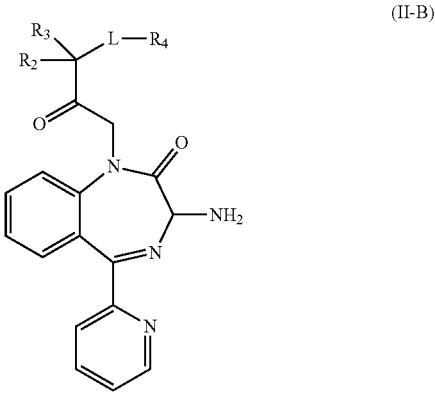

and the compound of formula (I-C) is a compound of formula (II-C):

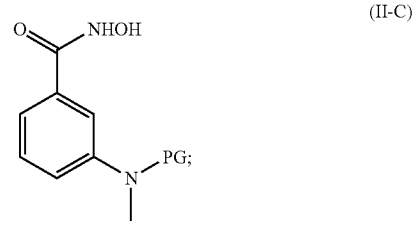

wherein PG is a protecting group.

11. The process of claim 1, wherein $R_2$ and $R_3$ together with the intervening carbon atom to which they are bonded, form a $C_{3-4}$ carbocyclic moiety, or wherein $R_2$ and $R_3$ are each, independently, H or $C_{1-2}$ alkyl; and L is a bond or $C_{1-3}$ alkylene.

12. The process of claim 1, wherein $R_2$ and $R_3$ are each, independently, $C_{1-2}$ alkyl and L is —$CH_2$—.

13. The process of claim 1, wherein $R_1$ is —$CH_2C(O)C(R_2)(R_3)$-L-$R_4$, $R_4$ is —$OR_5$ or —$SR_5$, $R_5$ is hydrogen, methyl or —$C(O)R_6$, and $R_6$ is optionally substituted aliphatic, heteroaliphatic, aromatic or heteroaromatic moiety.

14. The process of claim 1, wherein $R_6$ is substituted or unsubstituted $C_{1-6}$ aliphatic.

15. The process of claim 1, wherein $R_6$ is methyl.

16. The process of claim 1, wherein $R_4$ is —$OR_5$ and $R_5$ is —$C(O)R_6$.

17. The process of claim 1, wherein the compound of formula (I) is a compound selected from:

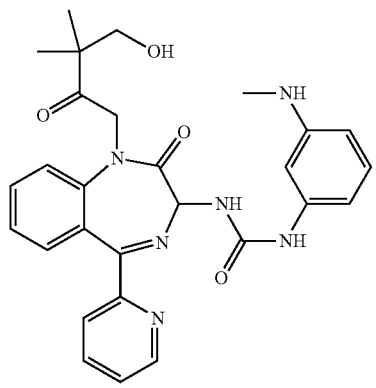

;

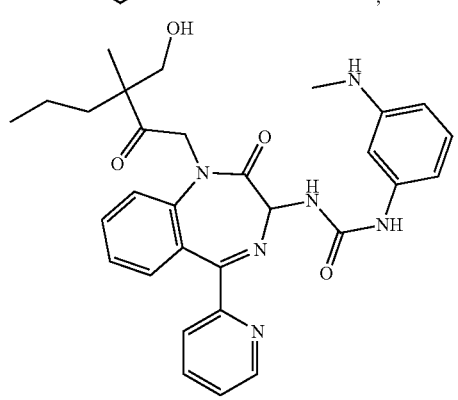

;

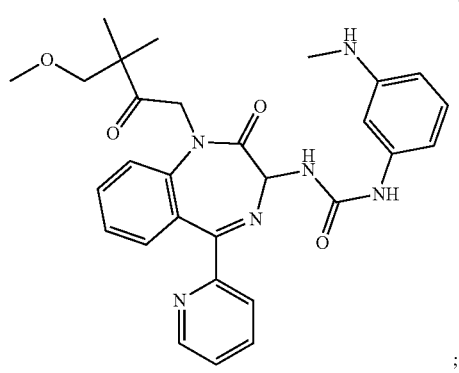

;

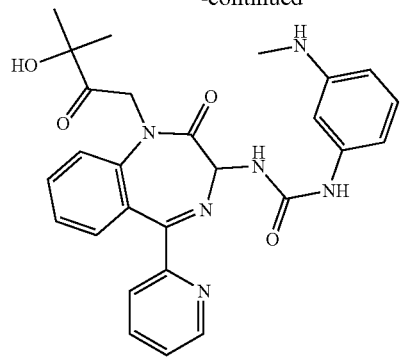

;

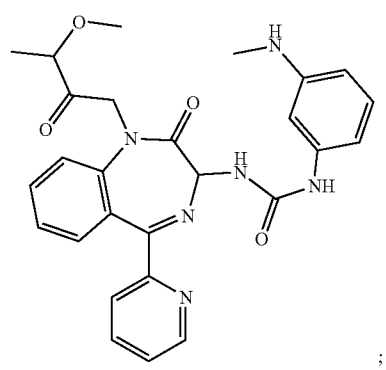

;

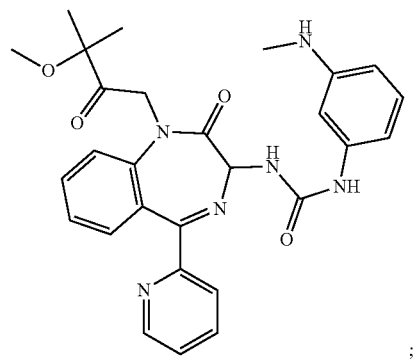

;

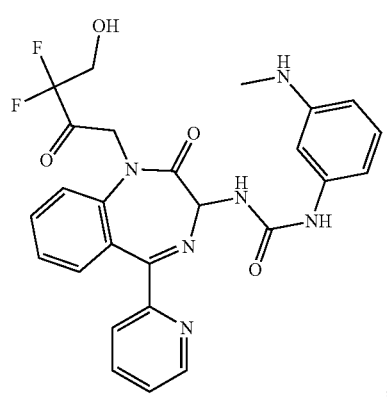

;

61
-continued
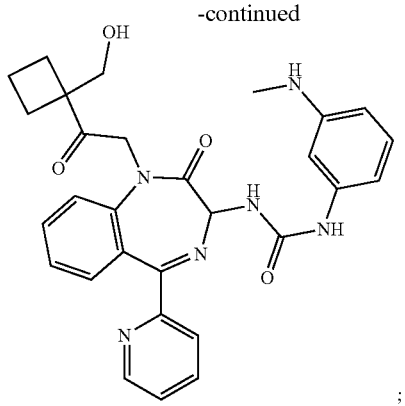
;
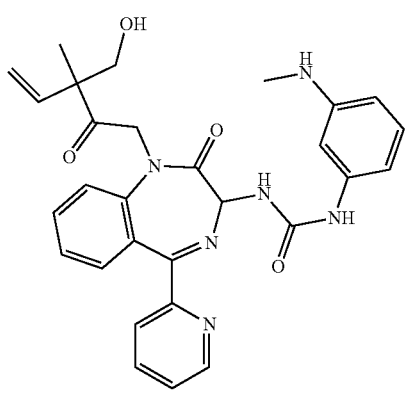
;
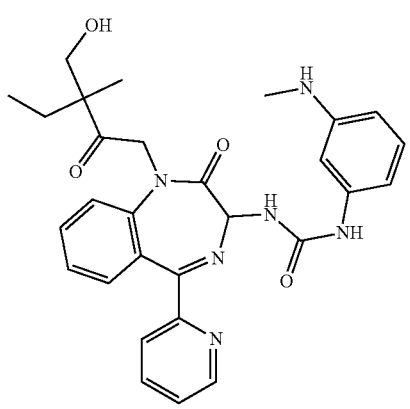
;
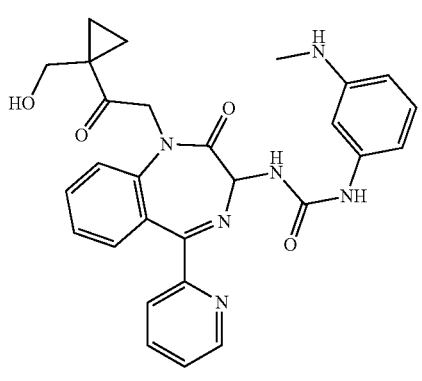
;
62
-continued
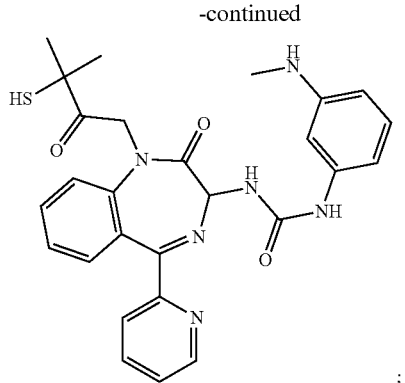
;
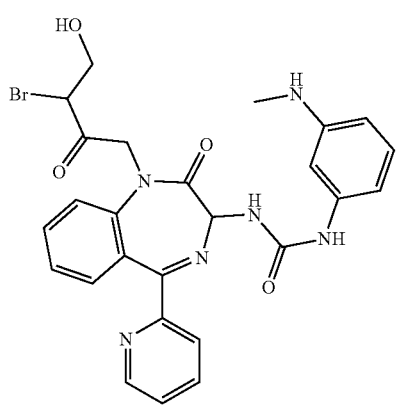
;
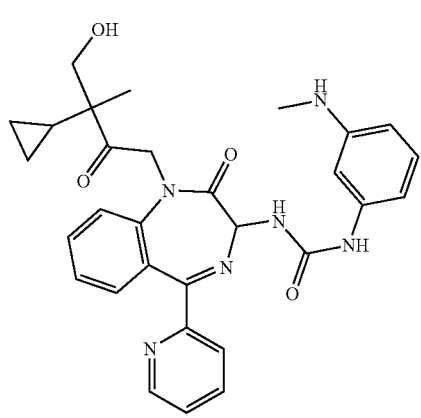
; and
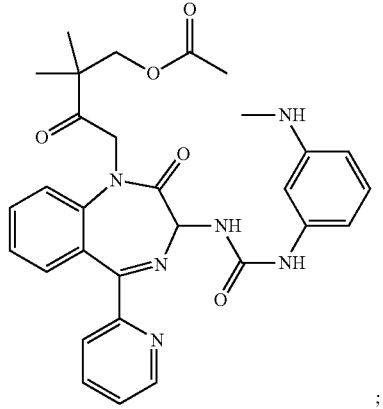 [SMILES: CNc1cccc(NC(=O)NC2N=C(c3ccccn3)c3ccccc3N(CC(=O)C(C)(C)COC(C)=O)C2=O)c1]
;
or a pharmaceutically acceptable salt thereof.

18. The process of claim 1, wherein the compound of formula (I) is a compound selected from:
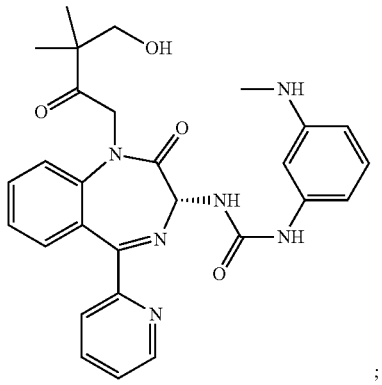
;
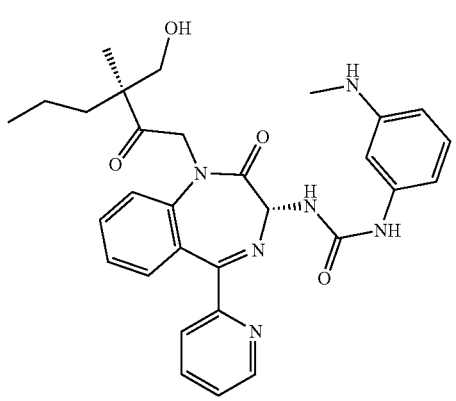
;
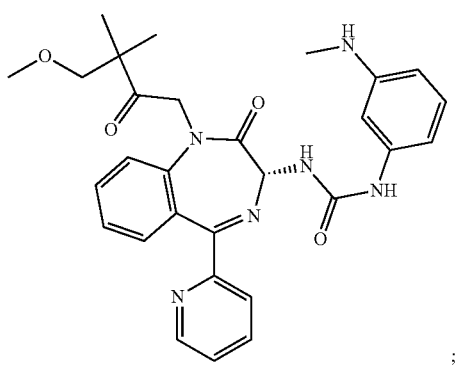
;
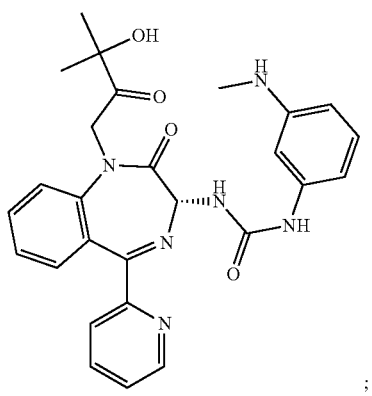
;
-continued
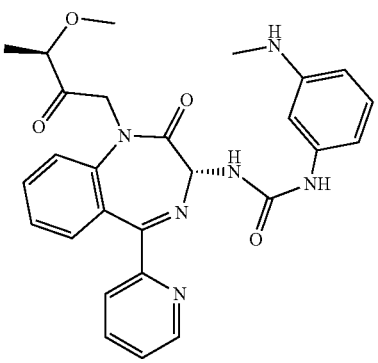
;
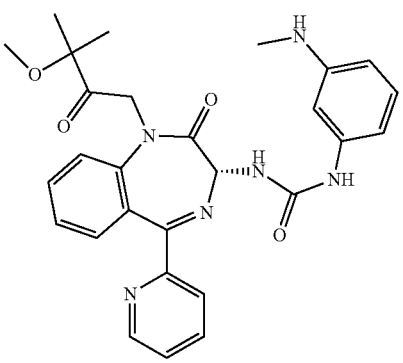
;
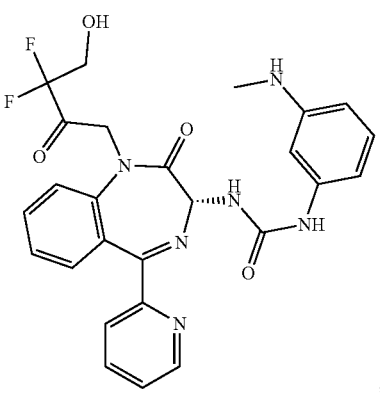
;
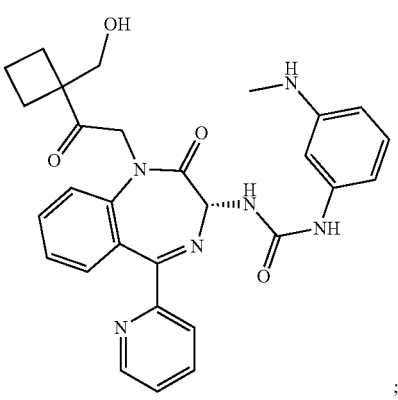
;

-continued
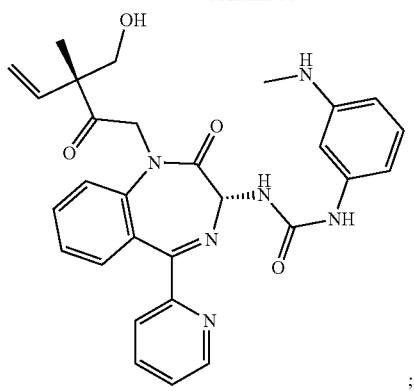
;
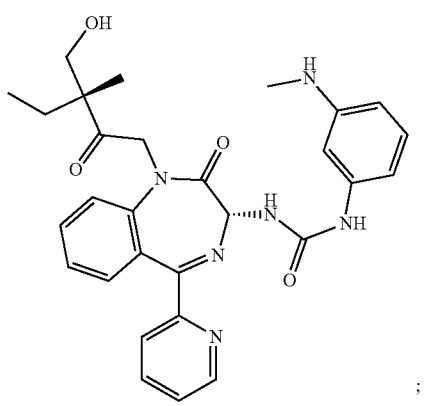
;
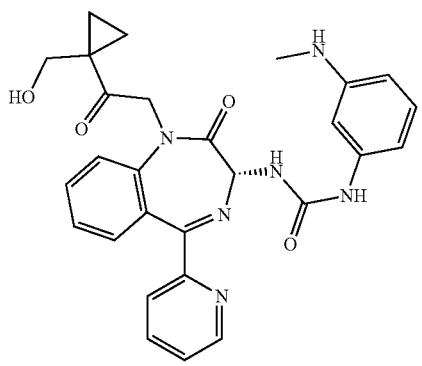
;
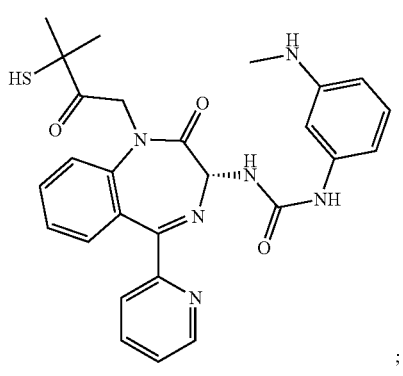
;
-continued
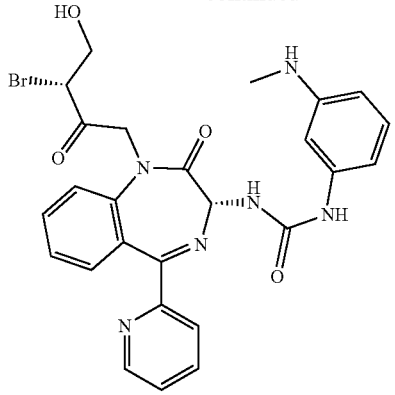
;
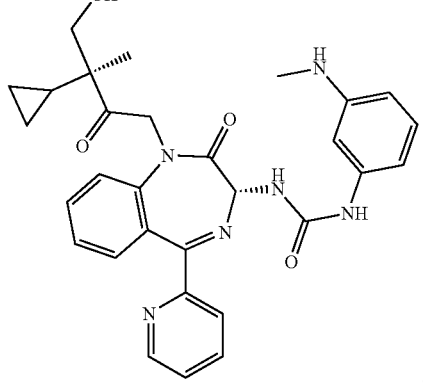
; and
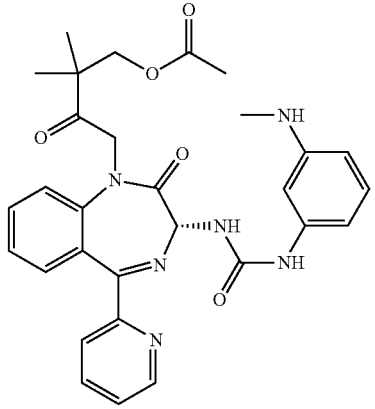
;
or a pharmaceutically acceptable salt thereof.
19. The process of claim 1, wherein the compound of formula (I) is a compound of formula (III):
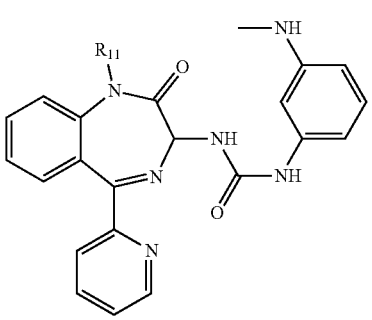
(III)
or a pharmaceutically acceptable salt thereof, wherein $R_{11}$ is selected from

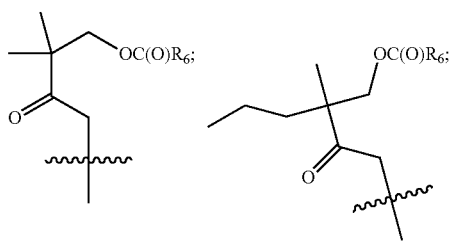
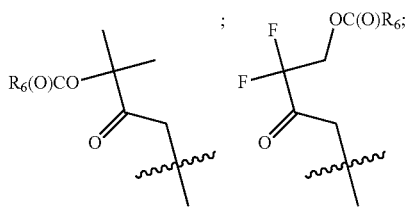
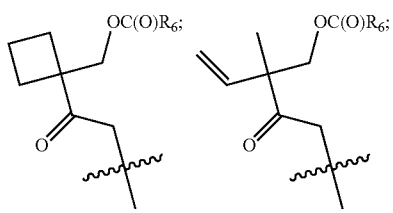
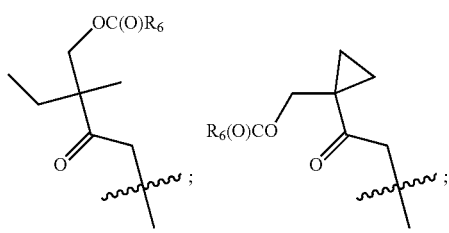
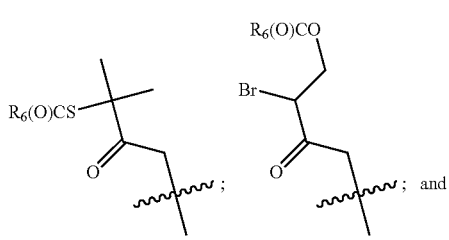
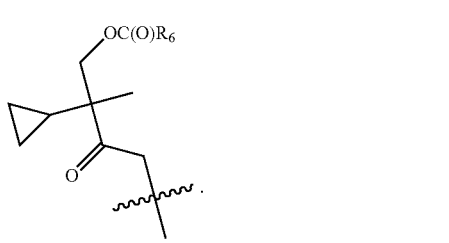
20. The process of claim 19, wherein the compound is a compound of formula (IV):
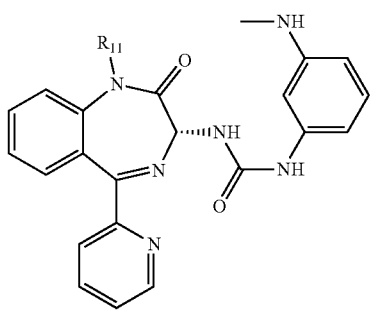
(IV)
or a pharmaceutically acceptable salt thereof.
21. The process of claim 1, wherein the compound of formula (I) is a compound (TR) or (TR-A):
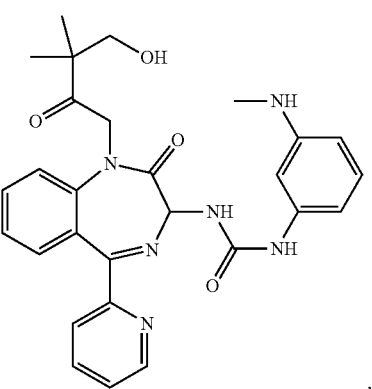
(TR)
,
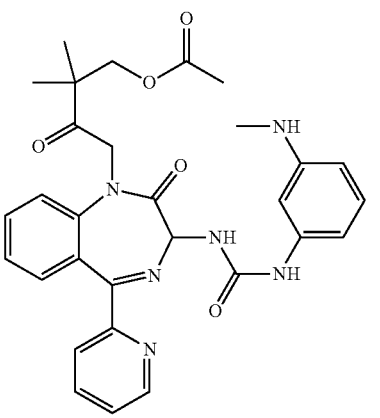
(TR-A)
or a pharmaceutically acceptable salt thereof.

22. The process of claim 21, wherein the compound is a compound (TR2) or (TR2-A):
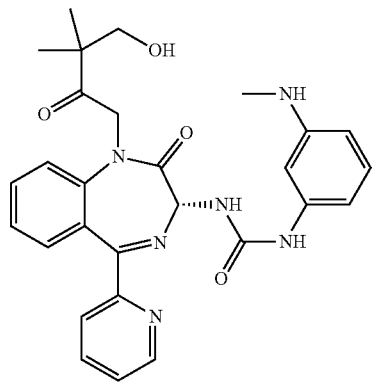
(TR2)
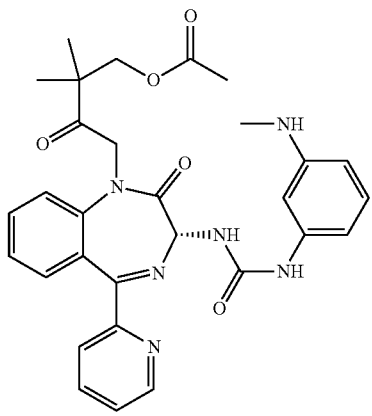
(TR2-A)
or a pharmaceutically acceptable salt thereof.
23. The process of claim 1, wherein the compound of formula (I) is YF476:
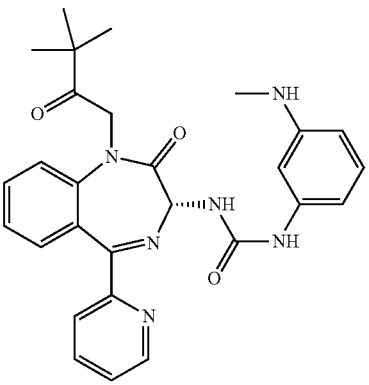
YF476
or a pharmaceutically acceptable salt thereof.
24. The process of claim 1, wherein the compound of formula (I) is the compound (TR-A):
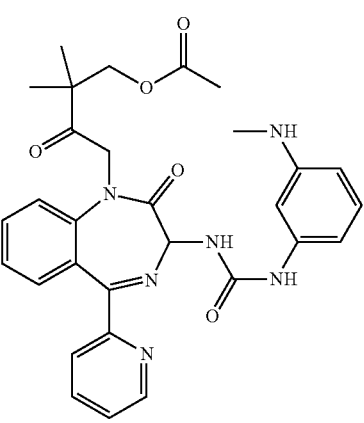
(TR-A)
or a pharmaceutically acceptable salt thereof.
* * * * *